United States Patent [19]
Suzuki

[11] Patent Number: 6,110,127
[45] Date of Patent: Aug. 29, 2000

[54] MEDICAL INSTRUMENT FOR USE IN COMBINATION WITH AN ENDOSCOPE

[75] Inventor: Takayuki Suzuki, Hachioji, Japan

[73] Assignee: Olympus Optical, Co., Ltd., Tokyo, Japan

[21] Appl. No.: 09/232,530

[22] Filed: Jan. 18, 1999

[30] Foreign Application Priority Data

Feb. 17, 1998 [JP] Japan ................................. 10-034784

[51] Int. Cl.[7] .................................................. A61B 10/00
[52] U.S. Cl. ..................... 600/565; 600/564; 606/170; 606/205; 604/22
[58] Field of Search ................................ 600/562, 564, 600/565, 566, 567; 606/106, 114, 115, 167, 170, 174, 205, 207; 604/22

[56] References Cited

U.S. PATENT DOCUMENTS

| 5,281,230 | 1/1994 | Heidmueller | 606/127 |
|---|---|---|---|
| 5,286,255 | 2/1994 | Weber | 600/565 |
| 5,471,992 | 12/1995 | Banik et al. | 600/564 |
| 5,538,008 | 7/1996 | Crowe | 606/170 |
| 5,645,075 | 7/1997 | Palmer et al. | 600/564 |
| 5,762,069 | 6/1998 | Kelleher et al. | 600/567 |
| 5,797,939 | 8/1998 | Yoon | 606/170 |
| 5,871,453 | 2/1999 | Banik et al. | 600/564 |
| 5,951,488 | 9/1999 | Slater et al. | 600/564 |
| 5,980,468 | 11/1999 | Zimmon | 600/567 |

FOREIGN PATENT DOCUMENTS

| 0 065 054 | 11/1982 | European Pat. Off. . |
|---|---|---|
| WO 95/08291 | 3/1995 | WIPO . |

*Primary Examiner*—Robert L. Nasser
*Assistant Examiner*—Charles Marmor, II
*Attorney, Agent, or Firm*—Frishauf, Holtz, Goodman, Langer & Chick, P.C.

[57] ABSTRACT

A medical instrument comprising an insertion section, an operation section connected to a proximal end of the insertion section, and sampling means. The insertion section has a sheath comprising an inner tube and an outer tube capable of moving back and forth in an axial direction with respect to the inner tube. The operation section is connected to a proximal end of the inner tube and has suction means for generating a suction force. The sampling means comprises a distal unit provided on a distal portion of the inner tube and having an opening through which a living tissue is to be drawn by the suction force applied from the inner tube, and cutting means for cutting a part of the living tissue drawn into the distal unit as the inner tube and the outer tube are moved relative to each other in an axial direction.

39 Claims, 11 Drawing Sheets

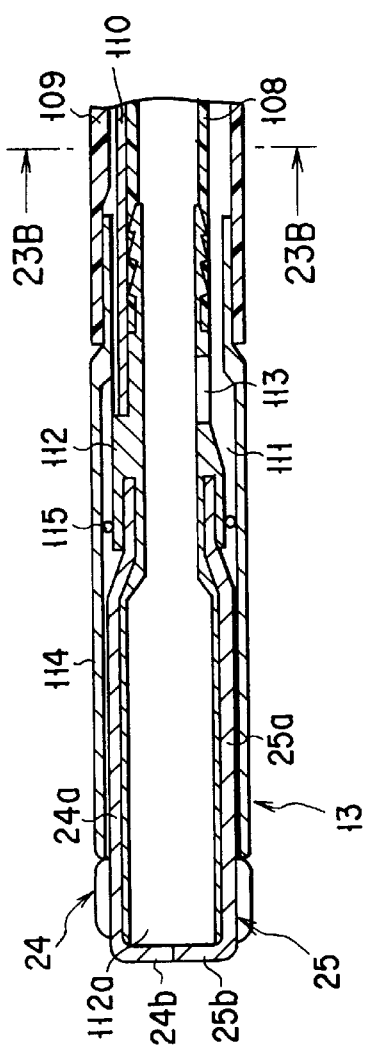
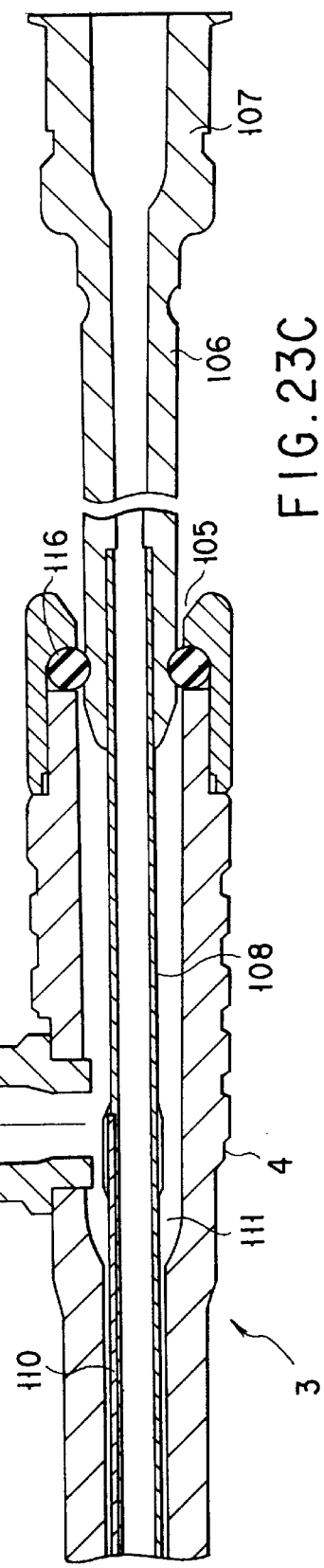

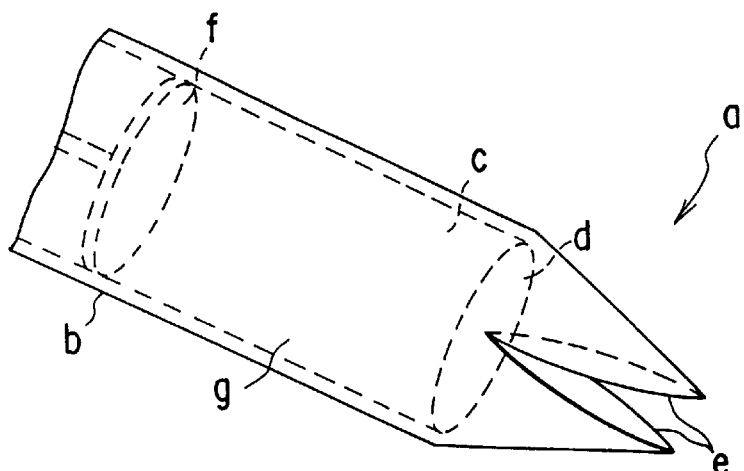
FIG. 24A
PRIOR ART
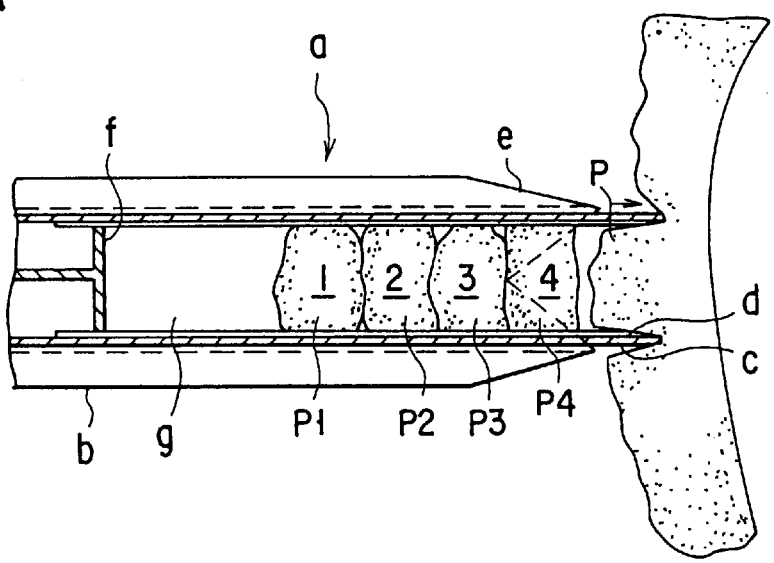
FIG. 24B
PRIOR ART
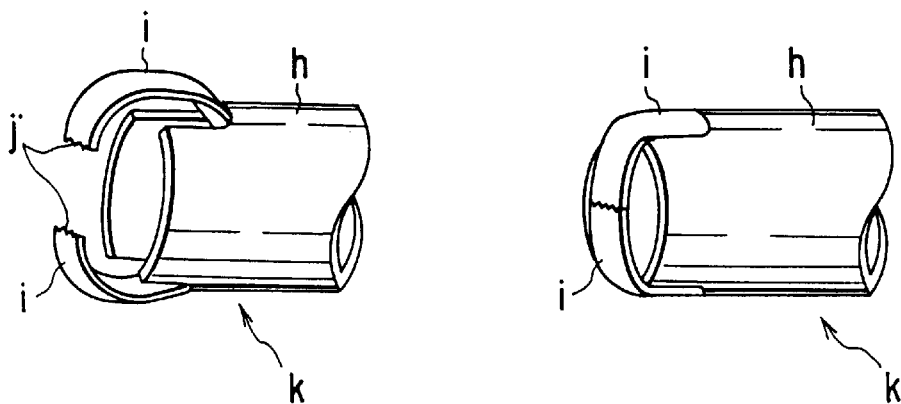
FIG. 24C
PRIOR ART
FIG. 24D
PRIOR ART

MEDICAL INSTRUMENT FOR USE IN COMBINATION WITH AN ENDOSCOPE

BACKGROUND OF THE INVENTION

The present invention relates to a medical instrument, which is designed, to be inserted into a patient's body through the instrument-guiding channel of an endoscope, already inserted into the patient's body, for cutting living tissues continuously and collecting a plurality of living-tissue samples.

Known as a medical instrument for sampling living tissues is the one disclosed in International Publication WO 95/08291. FIG. 24A is a diagram showing the main section of the instrument (a) disclosed in the publication. FIG. 24B is a diagram showing the medical instrument (a) in use. The medical instrument (a) comprises an outer sheath (b) and an inner sheath (c). The outer sheath (b) is flexible and can be inserted into a forceps channel of an endoscope. The inner sheath (c) is inserted in the outer sheath (b).

The inner sheath (c) has an opened distal end (d). The outer sheath (b) has a cutting means (e) at its distal end. The cutting means (e) is designed to cut living tissues (p). The cutting means (e) is biased in a direction, closing the distal end of the outer sheath (b). The cutting means (e) can cut living tissues (p) when it is moved, closing the opened distal end (d) of the inner sheath (c).

A retractor (f) is provided in the inner sheath (c) and can be moved in the axial direction of the inner sheath (c). The pieces (p1), (p2), (p3) and (p4) of the living tissue, cut by the cutting means (e), are sequentially guided into the inner sheath (c), from the opened distal end of the inner sheath (c). The retractor (f) pushes these pieces from the opened distal end of the inner sheath (c).

How the medical instrument (a) is used will be explained. First, the instrument (a) is inserted into a forceps channel of an endoscope, which has already been inserted to a patient's body. The instrument (a) is guided into the patient's body until its distal end reaches the target tissue (p) present in the patient's body. Then, as shown in FIG. 24B, the inner sheath (c) is thrust from the distal end of the outer sheath (b). The tissue (p) is thereby caught in the opened distal end (d) of the inner sheath (c).

The inner sheath (c) is then moved back in its axial direction and pulled into the outer sheath (b). As the inner sheath (c) is thus moved, the cutting means (e) cuts the tissue (p) because it is biased and closing the distal end of the outer sheath (b). The pieces (p1), (p2), (p3) and (p4) of the tissue (p), thus cut, are sampled into the tissue-storing space (g) provided in the inner sheath (c).

The tissue-sampling sequence described above is repeated several times. The pieces (p1), (p2), (p3) and (p4) sampled into the tissue-storing space (g) in the first sampling sequence are pushed toward the proximal end of the medical instrument (a) as other pieces of tissue are sampled. When the last tissue-sampling sequence completes, the instrument (a) is pulled out of the endoscope. The retractor (f) is pushed forward from the opened distal end (d) of the inner sheath (c). The pieces (p1), (p2), (p3), (p4) and so on, all sampled, are thereby collected.

European Patent EP 0 065 054 discloses a medical instrument (k), which is shown in FIGS. 24C and 24D. The instrument (k) comprises a hollow cylinder (h), and a cutting means (j). The cutting means (j) comprises a pair of arms (i) provided partly in the cylinder (h). The each arm (i) is formed by bending the distal ends of the members at right angles. When the arms (i) are pulled in the cylinder (h), and toward the proximal end thereof, the cutting means (j) cuts a living tissue (p).

When the medical instrument disclosed in International Publication W0095/08291 is used, the distal end of the inner sheath (c) must pierce the target living tissue (p), from the surface of the tissue (p). It is difficult, however, for the inner sheath (c) to plunge deep into the tissue (p) to sample a piece at a relatively deep position in the tissue (p). For doctors, too, it is hard to thrust the sheath (c) so deep into the tissue (p).

The opened distal end of the inner sheath (c) is sharpened enough to pierce the living tissue (p). Should the distal end of the inner sheath (c) touch any tissue other than the target tissue (p), it would damage the tissue. Much care should therefore be taken to manipulate the medical instrument (a).

With the medical instrument disclosed in European Patent EP 0 065 054 it is easy to sample a piece of the living tissue (p) if the cylinder (h) contacts the tissue (p), with its axis extending at right angles to the tissue (p). If the cylinder (h) is positioned with its axis extending at right angles or inclined to the living tissue (p), however, no part of the tissue (p) can be sampled. This is because no teeth are provided on the circumferential surface of the cylinder (h).

BRIEF SUMMARY OF THE INVENTION

The present invention has been made in view of the foregoing. The object of the invention is to provide a medical instrument for use in combination with an endoscope, which can safely and easily sample pieces of a living tissue at any depth, with simple manipulation, even if it is positioned with its axis extending at right angles or inclined to the living tissue.

To attain the object, a medical instrument according to the present invention comprises: a long, slender insertion section to be inserted into a body through the instrument channel of an endoscope; an operation section connected to a proximal end of the insertion section; and sampling means connected to a distal end of the insertion section and adapted to be driven by operating the operation section, for sampling a part of a living tissue present in the body. The insertion section has a sheath comprising an inner tube and an outer tube which can move back and forth in an axial direction, relative to the inner tube. The operation section is connected to a proximal end of the inner tube and has suction means for generating a suction force. The sampling means comprises a distal unit provided on a distal portion of the inner tube and having an opening through which a living tissue is to be drawn by the suction force applied from the inner tube, and cutting means for cutting a part of the living tissue drawn into the distal unit as the inner tube and the outer tube are moved relative to each other in an axial direction.

The medical instrument is used in the following manner. The insertion section is inserted into a patient's body, through the instrument channel of the endoscope. The distal unit on the inner tube is guided to a target living tissue present in the body. As the distal unit abuts on the living tissue, the opening of the distal unit is closed by the tissue. In this condition, the suction means is operated, applying a negative pressure in the distal unit. As a result, a part of the tissue is drawn into the distal unit through the opening, no matter whether the distal unit approaches the living tissue with its axis extending at right angles or inclined to the living tissue. The inner tube is moved in its axial direction, causing the cutting means to cut that part of the living tissue which has been drawn into the distal unit.

Therefore, the medical instrument can serve to sample a living tissue at any depth, with simple manipulation, even if the distal unit approaches the living tissue with its axis extending at right angles or inclined to the tissue.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

FIG. 23A is a longitudinal sectional view of the distal end portion of a medical instrument according to the thirteenth embodiment of the invention;

FIG. 23B is a cross-sectional view taken along line 23B—23B in FIG. 23A;

FIG. 23C is a longitudinal sectional view of the operation section of the thirteenth embodiment;

FIG. 24A is a perspective view of a conventional instrument for sampling living tissues;

FIG. 24B is a longitudinal sectional view of the conventional instrument, showing the pieces of tissues being sampled;

FIG. 24C is a perspective view of the distal end portion of another conventional instrument, showing the cutting means in the opened position; and FIG. 24D is a perspective view of the distal end portion of the conventional instrument in FIG. 24C, showing the cutting means in the closed position.

DETAILED DESCRIPTION OF THE INVENTION

Figure 1A:
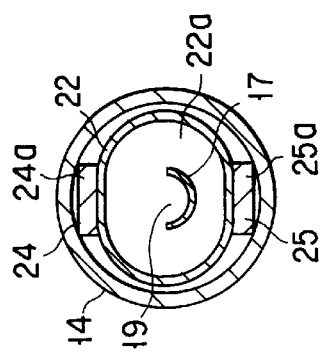
FIG. 1A is a perspective view of a medical instrument for use in combination with an endoscope, which is a first embodiment of the present invention.

The first embodiment of the invention will be described with reference to FIGS. 1A to 1C, FIG. 2, FIGS. 3A and 3B, FIGS. 4 and 5, FIGS. 6A to 6C, and FIGS. 7 to 9. The first embodiment is a medical instrument 1 for use in combination with an endoscope. As shown in FIG. 1A, the instrument 1 comprises an insertion section 2 and an operation section 3. The insertion section 2 is long and slender and can be inserted into a forceps channel (instrument-guiding channel, not shown) of an endoscope. The operation section 3 is secured to the proximal end of the insertion section 2.

The operation section 3 comprises a casing 4, which is a hollow cylinder having a substantially circular cross section. The casing 4 has a suction port 5 protruding from the end connected to the insertion section 2. An external suction means 6 is provided, which may be an electric driven pump, a manual pump, a rubber ball, or a large syringe. The means 6 has a connection tube 6a, which can be connected to the suction port 5.

A finger ring 7 is provided on the proximal end of the casing 4. A slider 8 is mounted on that portion of the casing 4 which extends between the suction port 5 and the finger ring 7. The slider 8 can move in the axial direction of the operation section 3.

The insertion section 2 comprises a thin, long flexible sheath 9 that is so durable as to remain integrated over repeated manipulation of the medical instrument 1. The sheath 9 is composed of durable members. For example, the sheath 9 comprises an outer tube 10 and an inner tube 11 as is illustrated in FIG. 1B. The outer tube 10 is a tightly wound coil, and the inner tube 11 is movably inserted in the outer tube 10. The tubes 10 and 11 constitute a double tube.

The inner tube 11 is airtight, made of air-impermeable material such as a resin (e.g., tetrafluoroethylene, polyethylene, or the like) or a metal material having very high elasticity. An operation wire 12 extends in the inner tube 11, along the axis thereof and over the entire length thereof.

A sampling means 13 is provided at the distal end of the sheath 9. The sampling means 13 comprises a distal pipe 14 and a distal unit 15. The distal pipe 14 is fixed to the distal end of the outer tube 10. The distal unit 15 is removably connected to the distal end of the inner tube 11.

A wire coupling 16 is secured to the distal end of the inner tube 11. The proximal end of the wire coupling 16 holds the distal end of the operation wire 12. The distal end of the wire coupling 16 is secured to the proximal end of a suction pipe 17. The coupling 16 has a hole 18 located at the rear of the junction between the coupling 16 and the suction pipe 17. The hole 18 connects the interior of the suction pipe 17 to the interior of the inner tube 11. The distal pipe 14, wire coupling 16 and suction pipe 17 are made of metal such as stainless steel or resin such as polysulfone, polyphenylsulfone or polycarbonate.

Figure 2:
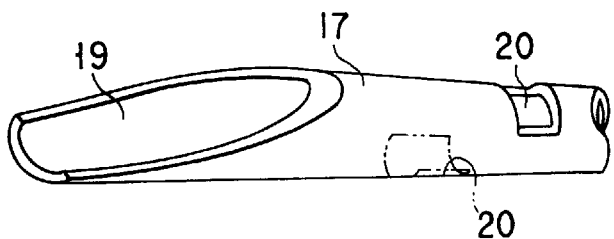
FIG. 2 is a perspective view showing the main part of the suction pipe incorporated in the first embodiment shown in FIG. 1A.

As shown in FIG. 2, the suction pipe 17 has a distal end cut slantwise. The pipe 17 therefore has an elliptical opening 19, the major axis of which inclines to the axis of the pipe 17. The suction pipe 17 has a plurality of side holes 20 in its distal portion.

The wire coupling 16 has a male-threaded distal end 21. The male-threaded end 21 is mounted on the proximal portion of the suction pipe 17. The proximal portion of the distal unit 15 abuts on the male-threaded end 21.

The distal unit 15 has a storage tube 22. The storage tube 22 provide a storage space 22a, in which sampled pieces of tissue may be stored. The proximal end of the storage tube 22 is connected to a hollow cylindrical coupling 23. The coupling 23 has a screw hole 23a in its proximal end. It is in the screw hole 23a that the male-threaded end 21 of the wire coupling 16 is held in screw engagement.

Figure 1C:
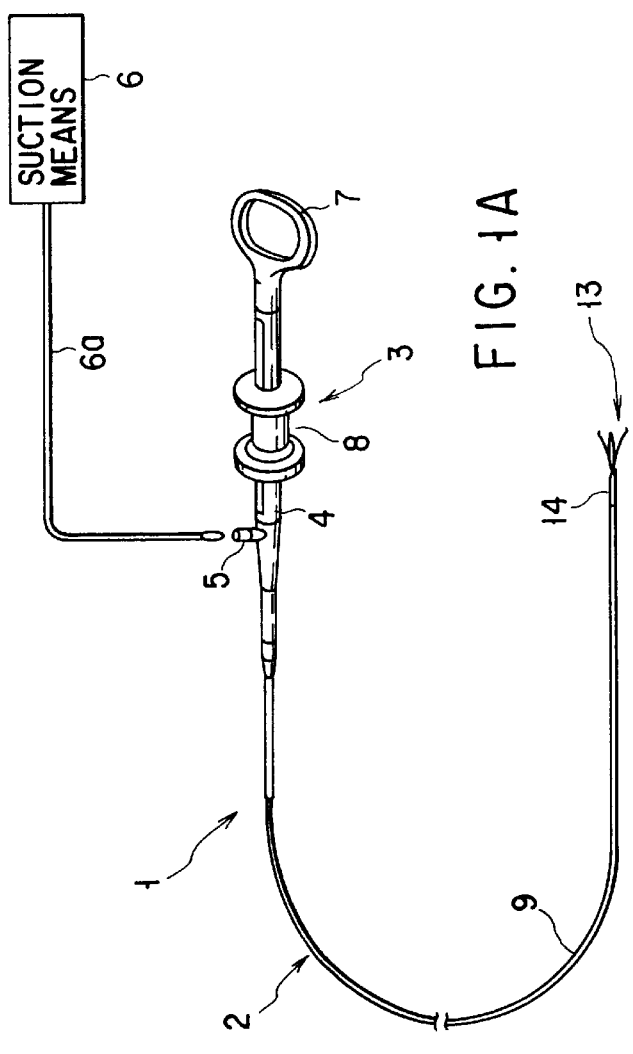
FIG. 1C is a cross-sectional view taken along line IC—IC in FIG. 1B.
Figure 1B:
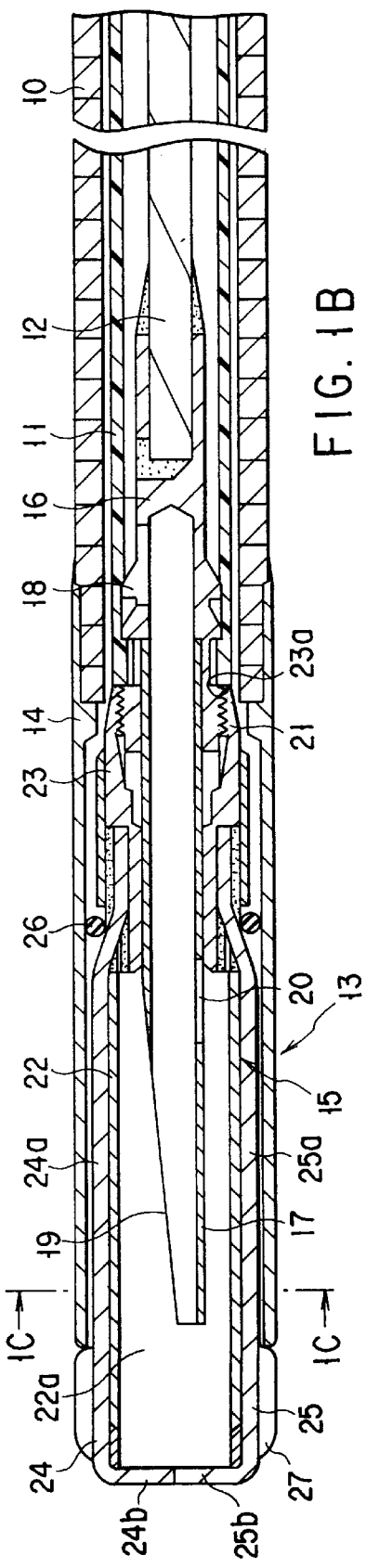
FIG. 1B is a longitudinal sectional view of the first embodiment shown in FIG. 1A.

As shown in FIG. 1C, the storage tube 22 has an oblate cross section. The tube 22 therefore has two flat parts that oppose each other. The tips (cutting means) 24 and 25 of a forceps are mounted on the flat parts of the storage tube 22. Both forceps tips 24 and 25 may be made of very elastic alloy such as stainless spring steel or nickel-titanium alloy. Alternatively, the tips 24 and 25 may be made of hard resin such as ABS resin or polycarbonate.

The forceps tips 24 and 25 are connected to the distal ends of elastic arms 24a and 25a, respectively. The proximal ends of the arms 24a and 25a are secured to the outer circumference of the coupling 23 by means of soldering, spot welding, caulking or adhesion, or by means of screws.

Figure 4:
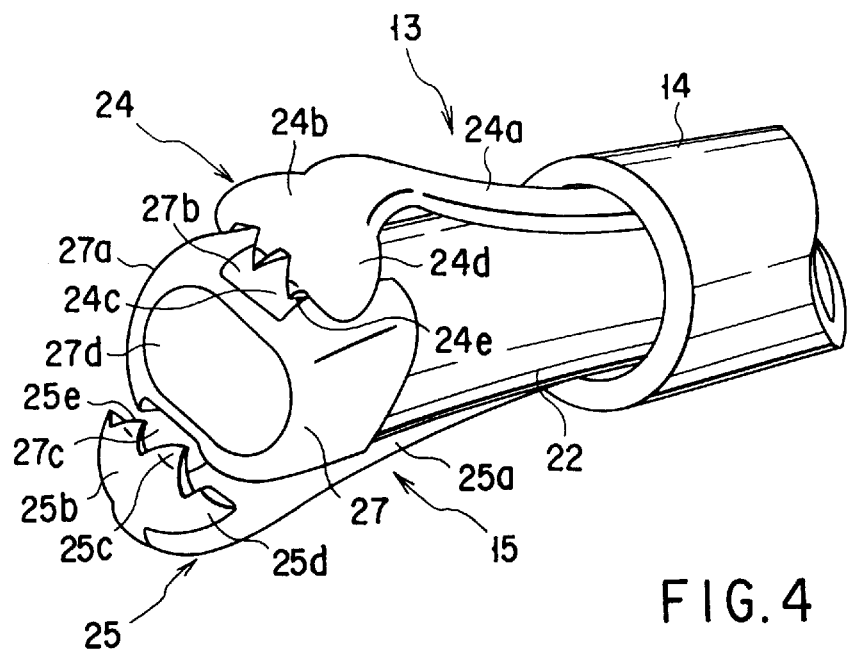
FIG. 4 is a perspective view showing the distal blades of the first embodiment shown in FIG. 1A, which are in the opened positions.
Figure 5:
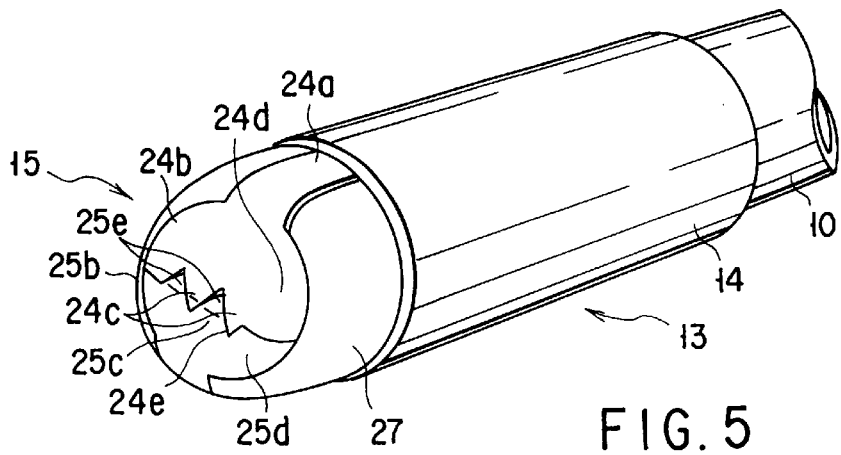
FIG. 5 is a perspective view depicting the distal blades of the first embodiment shown in FIG. 1A, which are in the closed positions.

The elastic arms 24a and 25a have their distal portions projecting forward from the storage tube 22. The distal portions of the arms 24a and 25a are bent at a right angle toward the axis of the storage tube 22, respectively forming blades (cutting portion) 24b and 25b. As shown in FIG. 4, the blade 24b consists of saw teeth 24c and a rounded part 24d. Similarly, the blade 25b consists of saw teeth 25c and a rounded part 25d. The saw teeth 24c have a sharp edge 24e each, and the saw teeth 25c have a sharp edge 25e each. The edges 24e and 25e meet each other when the blades 24b and 25b are moved into their closed position as is shown in FIG. 5.

The elastic arms 24a and 25a are so biased that the blades 24b and 25b are spaced apart from each other, each at some distance from the axis of the storage tube 22. The elastic arms 24a and 25a may be connected at their proximal end, forming an integral member which is mounted on the outer circumferential surface of the storage tube 22.

The forceps tips 24 and 25 can be made by processing plates of the above-exemplified materials, for example by photo-etching, discharge wire-cutting, or ordinary cutting. They may be formed by plasticity secondary processing performed by a press or the like. The forceps tips 24 and 25 can, therefore, be manufactured in large quantities and at low cost.

The distal unit 15 has a seal member 26, such as an O-ring. The seal member 26 is mounted on the junction between the hollow cylindrical coupling 23 and the proximal ends of the elastic arms 24a and 25a. A distal frame 27, which is shaped like a ring, is mounted on the distal portion of the storage tube 22. The frame 27 has a larger outer diameter than the storage tube 22. The outer circumferential surface of the frame 27 is flush with that of the distal pipe 14. The distal frame 27 has rounded distal end 27a and two cutouts 27b and 27c. The elastic arm 24a of the forceps tip 24 and the elastic arm 25a of the forceps tip 25 are fitted in the cutouts 27b and 27c, respectively, as shown in FIG. 5, when the blades 24b and 25b are moved into their closed position.

The distal frame 27 has an opening 27d in its distal end. The opening 27d communicates with the storage space 22a provided in the storage tube 22. The opening 27d is elliptical, not connected to the cutout 27b or 27c. The junction between the opening 27d and the storage space 22a gradually flares toward the opening 27d. The storage tube 22 and the distal frame 27 are made of metal such as stainless steel, or resin such as polysulfone, polyphenylsulfone or polycarbonate. Although the tube 22 and the frame 27 are complicated in shape, they may be formed by injection molding or similar process.

The distal unit 15, including the elastic arms 24a and 25a, have an outer diameter smaller than the inner diameter of the distal pipe 14. The distal unit 15 can therefore be stored in the distal pipe 14, together with the elastic arms 24a and 25a. The proximal end of the outer tube 10 is secured to the distal end of the casing 4 of the operation section 3. The inner tube 11 and the operation wire 12 have their proximal ends secured to the slider 8 in the operation section 3.

When the slider 8 is moved in the axial direction of the operation section 3, the inner tube 11 and the operation wire 12 move with respect to the outer tube 10, in the same direction as the slider 8. As the tube 11 and wire 12 move, the blades 24b and 25b are moved into the opened positions or the closed positions. When moved into the closed position, the blades 24b and 25b clamp and cut a living tissue.

More precisely, when the slider 8 is moved toward the proximal end of the operation section 3, the inner tube 11 and the operation wire 12 pull the distal unit 15 and both elastic arms 24a and 25a into the distal pipe 14. As the arms 24a and 25a are pulled into the distal pipe 14, they bend toward the axis of the instrument 1, in spite of their elasticity. As a result, the blades 24b and 25b move forward, sliding on the outer surface of the distal frame 27. The blades 24b and 25b move forward until each saw-tooth edge 24e of the blade 24b and the corresponding saw-tooth edge 25e of the blade 25b abut on each other. If the blades 24b and 25b hold a living tissue between them, they can exert a sufficient cutting force on the living tissue.

Figure 3A:
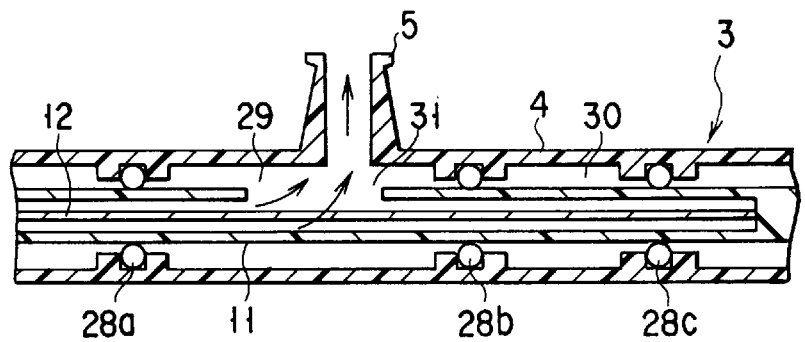
FIG. 3A is a longitudinal sectional view explaining how air is drawn from the inner tube incorporated in the first embodiment of FIG. 1A.
Figure 3B:
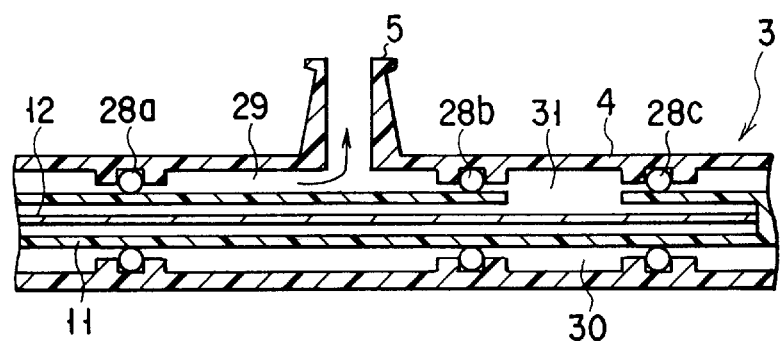
FIG. 3B is a longitudinal sectional view showing the inner tube from which air is no longer drawn.

As illustrated in FIGS. 3A and 3B, three O-rings 28a, 28b and 28c are fitted in the hollow cylindrical casing 4. The O-rings 28a, 28b and 28c are arranged at appropriate intervals in the axial direction of the medical instrument 1. The O-rings 28a, 28b and 28c are mounted on the outer circumferential surface of the inner tube 11, in sliding contact therewith. A first airtight chamber 29 is provided between the O-rings 28a and 28b, and a second airtight chamber 30 is provided between the O-rings 28b and 28c. The first airtight chamber 29 communicates with the suction port 5 of the operation section 3.

A suction hole 31 is made in the proximal portion of the inner tube 11. The suction hole 31 is moved between the first and second positions shown in FIGS. 3A and 3B, respectively, as the slider 8 is moved back and forth in the axial direction of the operation section 3. More specifically, when the slider 8 is moved to its fore position, the suction hole 31 moves to the first position (FIG. 3A), where the hole 31 communicates with the first airtight chamber 29. As long as the slider 8 is held at the fore position, the distal unit 15 remains exposed, projecting from the distal pipe 14 as is shown in FIG. 4. When the slider 8 is moved to its rear position, the suction hole 31 is moved to the second position (FIG. 3B), where the hole 31 communicates with the second airtight chamber 30. As long as the slider 8 is held at the rear position, the distal unit 15 remains held in the distal pipe 14 as is shown in FIG. 5.

Figure 8:
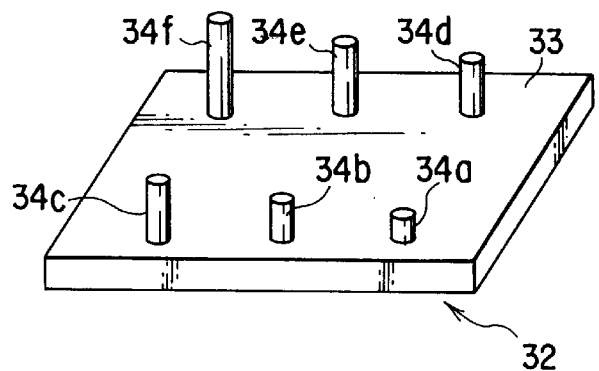
FIG. 8 is a perspective view of a jig designed to hold the pieces of tissue which have been sampled by using the first embodiment.

FIG. 8 shows a jig 32 designed to hold the pieces of tissue which have been sampled by using the medical instrument 1 described above. To collect the tissue pieces from the instrument 1, the distal unit 15 is removed from the distal end of the inner tube 11. Then, the tissue pieces sampled are taken out of the storage tube 22 of the distal unit 15. The tissue pieces, thus collected, are held on the jig 32.

As illustrated in FIG. 8, the jig 32 is composed of a base 33 and six projections 34a to 34f. The base 33 is a flat plate. The projections 34a to 34f stand upright on the base 33. The number of the projections is not limited to six; more or less projections may be provided on the base 33. The projections 34a to 34f have a diameter smaller than the inner diameter of the storage tube 22 of the distal unit 15. They can therefore be inserted into the storage tube 22. They have different lengths, each being shorter than the preceding one. The shortest projection 34a is about 1 to 3 mm long, and the longest projection 34f is as long as the distal unit 15.

How a doctor manipulates the medical instrument 1 to sample pieces of tissue will be explained. First, the connection tube 6a of the suction means 6 is connected to the suction port 5, and the suction means 6 is operated. In this condition, the doctor moves the slider 8 toward the proximal end of the operation section 3. The distal unit 15 is thereby pulled into the distal pipe 14, bending both forceps tips 24 and 25 into their closed positions. As the distal unit 15 is pulled into the distal pipe 14, the inner tube 11 is moved, bringing the suction hole 31 to the second position (FIG. 3B). The suction hole 31 comes to communicate with the second airtight chamber 30. The negative pressure (i.e., suction force generated by the suction means 6) is not applied to the inner tube 11.

The distal end of the distal pipe 14 is held, abutting on the proximal end of the distal frame 27. The insertion section 2 in this condition is inserted into a body cavity of the patient through the forceps channel of an endoscope, already inserted into the body cavity. To state more precisely, the doctor manipulates the endoscope or the instrument 1, guiding the sampling means 13 provided at the distal end of the insertion section 2 to the mucous membrane which is the target tissue, while observing the interior of the body cavity through the endoscope. When the sampling means 13 reaches the mucous membrane, the doctor moves the slider 8 forward. The distal unit 15 is thereby projected from the distal pipe 14, moving the forceps tips 24 and 25 to their opened positions, as is illustrated in FIG. 4. At the same time, the suction hole 31 is moved from the second position to the first position (FIG. 3A). At the first position the hole 31 communicates with the first airtight chamber 29. In this condition, the negative pressure (the suction force generated by the means 6) is applied in the inner tube 11.

Figure 6A:
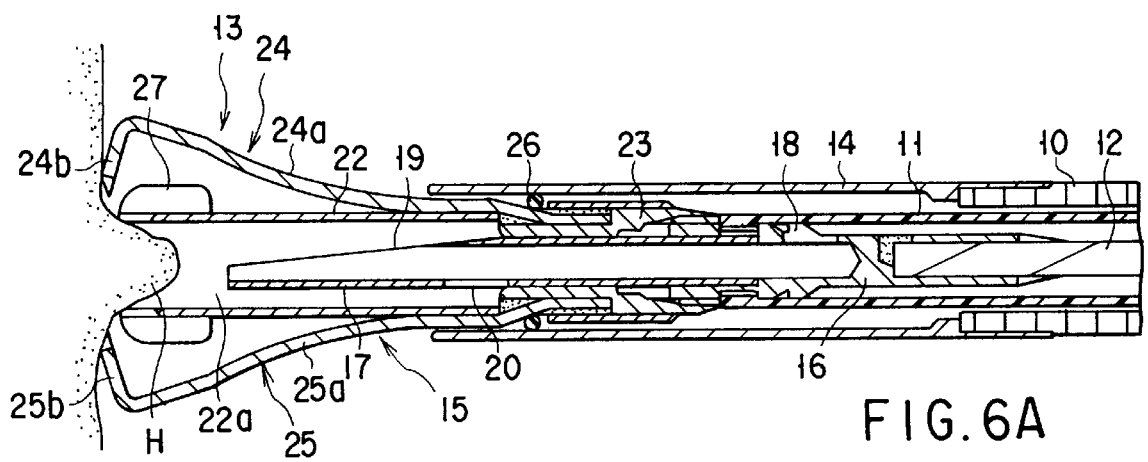
FIG. 6A is a longitudinal sectional view of the first embodiment, illustrating how a part of a living tissue is drawn into the inner tube through the opened distal end of the inner tube.

Then, the doctor moves the medical instrument 1, setting the distal frame 27 into contact with the mucous membrane H. A part of the membrane H is therefore drawn into the storage tube 22 through the opening 27d of the frame 27 as is shown in FIG. 6A, by virtue of the negative pressure applied in the inner tube 11.

Figure 6B:
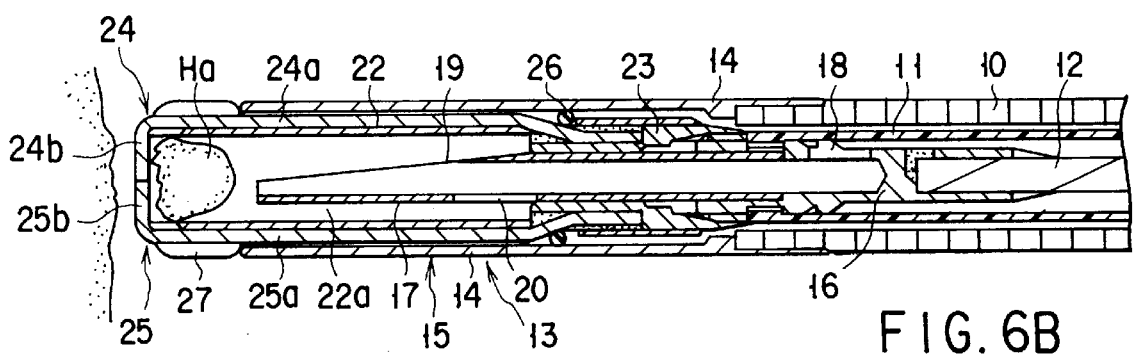
FIG. 6B is a longitudinal sectional view of the first embodiment, explaining how the part of the tissue is cut after it is drawn into the inner tube.

The doctor moves the slider 8 toward the proximal end of the operation section 3, pulling the distal unit 15 into the distal pipe 14 and moving the forceps tips 24 and 25 to their closed positions. The blades 24b and 25b clamp that part of the mucous membrane H which has been drawn into the storage tube 22. Eventually, as shown in FIG. 6B, the blades 24b and 25b cut this part of the membrane H. This part of the membrane, or a piece Ha, is held in the storage tube 22 and located near the opening 27d of the distal frame 27.

Meanwhile, the suction hole 31 of the inner tube 11 moves to the first position (FIG. 3B) as the slider 8 is moved toward the proximal end of the operation section 3. The hole 31 comes to communicate with the second airtight chamber 30, and the negative pressure is no longer applied in the inner tube 11.

Next, the doctor manipulates either the endoscope or the instrument 1, thereby guiding the sampling means 13 to another part of the mucous membrane H, which is to be sampled next. When the sampling means 13 reaches the other part of the membrane H, the doctor moves the slider 8 forward. The distal unit 15 is thereby projected from the distal pipe 14, moving the forceps tips 24 and 25 to their opened positions. The suction hole 31 is simultaneously moved to the first position (FIG. 3A).

Figure 6C:
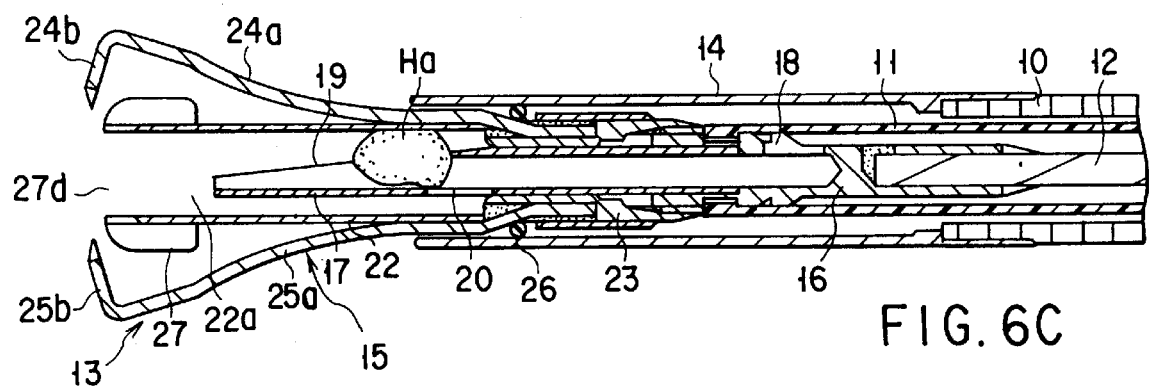
FIG. 6C is a longitudinal sectional view of the medical instrument, explaining how the part of the tissue is held in the suction pipe by suction force after it is cut.

At the first position the hole 31 communicates with the first airtight chamber 29. Hence, the negative pressure (the suction force generated by the means 6) is applied in the inner tube 11. By virtue of the negative pressure, the sampled piece Ha moves deeper in the storage tube 22 from the opening 27d of the distal frame 27 to the proximal end of the elliptical opening 19 of the suction pipe 17. The sampled piece Ha is eventually held at the proximal end of the elliptical opening 19 as is illustrated in FIG. 6C. Although the elliptical opening 19 is partly closed by the sampled piece Ha, the negative pressure is applied in the opening 27d of the distal frame 27 through the side holes 20 made in the suction pipe 17.

In this condition, the distal frame 27 is moved into abutment with the next target mucous membrane H. This mucous membrane H is drawn into the storage tube 22 through the opening 27d of the distal frame 27, in the same way as the first mucous membrane was taken into the storage tube 22. Then, the doctor pulls the slider 8 toward the proximal end of the operation section 3, in the same way as he pulled it for the first time, thereby cutting a second piece Hb from the membrane H.

Figure 7:
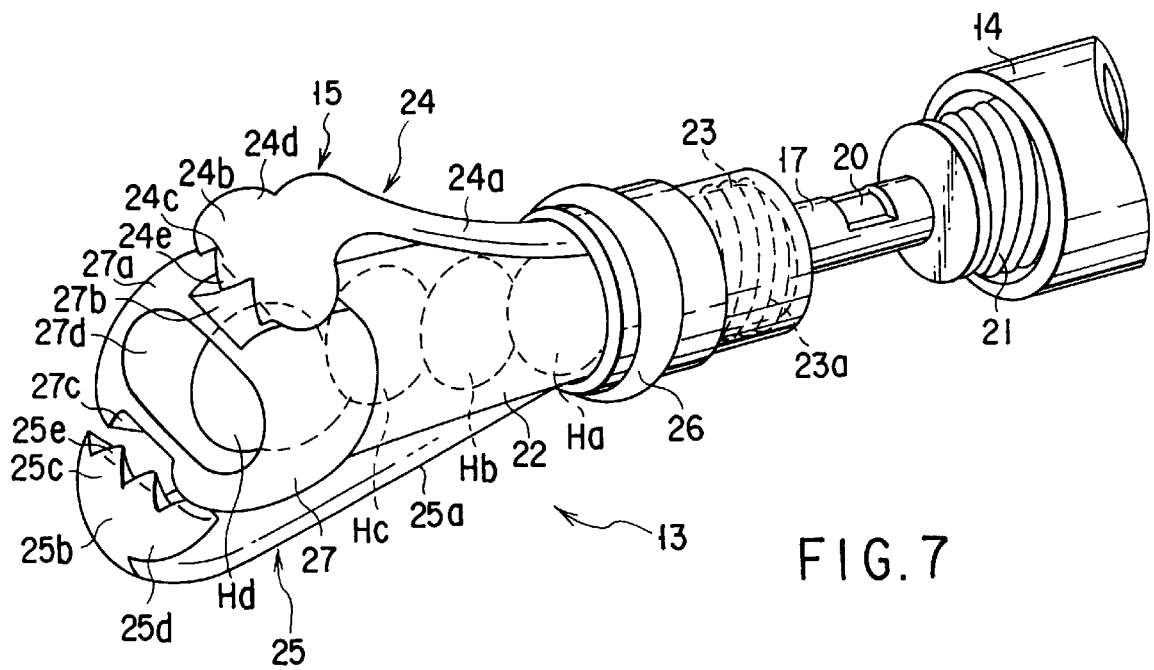
FIG. 7 is a perspective view of the distal portion of the first embodiment, showing the distal unit removed from the distal end of the inner tube.

Thereafter, the doctor may repeats the above-described sequence of manipulating the medical instrument 1, thereby cutting other pieces Hc, Hd, . . . of the membrane H. As a result, the pieces Ha, Hb, Hc, Hd, . . . are stored in the storage space 22a of the tube 22, arranged in the order mentioned as is illustrated in FIG. 7. The sequence of manipulating the medical instrument 1 can be further repeated until the storage space 22a is completely filled with sampled pieces of the membrane H, inhibiting the application of the negative pressure in the opening 27d of the distal frame 27.

After taking the pieces Ha, Hb, . . . of the membrane H into the storage tube 22, the doctor pulls the medical instrument 1 out of the forceps channel of the endoscope. Then, he or she removes the suction means 6 from the suction port 5, and moves the slider 8 toward the distal end of the operation section 3, projecting the distal unit 15 from the distal pipe 14. This done, the doctor rotates the distal unit 15, releasing the male-threaded end 21 of the wire coupling 16 from the screw hole 23a of the distal unit 15, and further removes the distal unit 15 from the distal end of the inner tube 11.

Figure 9:
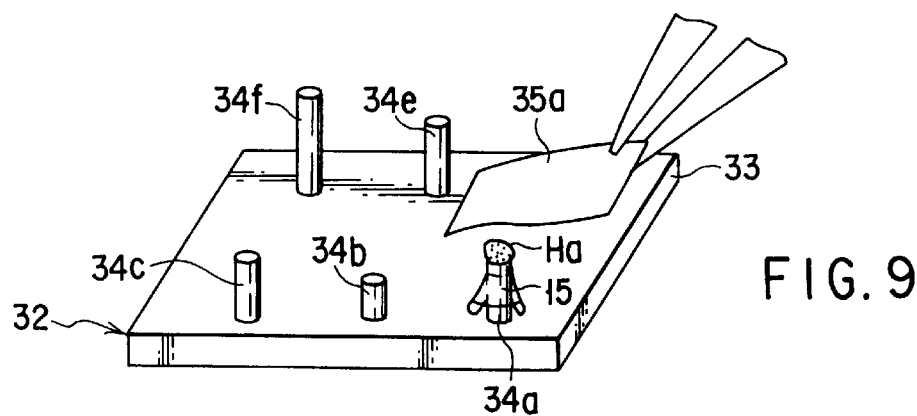
FIG. 9 is a perspective view of the jig, explaining how a piece of tissue sampled is collected and held on the jig.

After removing the distal unit 15 from the inner tube 11, the doctor collects the pieces Ha, Hb, . . . of the membrane H from the storage space 22a of the tube 22, by using the jig shown in FIG. 8. More specifically, the doctor inserts the shortest projection 34a of the jig 32 into the storage tube 22 of the distal unit 15 through the opening 27d of the distal frame 27. The first piece Ha is thereby pushed from the proximal end of the storage tube 22 as is illustrated in FIG. 9. The first piece Ha is attracted onto a first filter sheet 35a. Thus, the first piece Ha is sampled and collected.

Further, the doctor inserts the next shortest projection 34b into the storage tube 22, pushing the second piece Hb from the storage tube 22, and places a second filter sheet on the second piece Hb, thereby sampling and collecting the second piece Hb. Still further, he or she repeats a similar sequence of inserting a projection into the tube 22 and placing a filter sheet, until all other pieces Hc, Hd . . . of the membrane H are sampled and collected, one after another. Hence, the pieces Ha, Hb, . . . are collected and sampled in the order they have been cut from the membrane H.

The medical instrument 1 described above is advantageous in the following respects.

As indicated above, the insertion section 2 is inserted into the patient's body cavity through the forceps channel of the endoscope until the distal frame 27 of the distal unit 15 coupled to the distal end of the inner tube 11 abuts the target mucous membrane H, while the suction means connected to the medical instrument 1 is operating. It is therefore possible to draw a part of the membrane H into the storage tube 22 through the opening 27d of the distal frame 27 and hold the same in the storage tube 22. No needles must be provided on the distal end of the distal frame 27 to hold the membrane H as in the conventional medical instrument. In other words, the distal frame 27 need not be sharpened at all. Hence, the medical instrument 1 enables doctors to sample pieces of the target membrane, without damaging anything in the body cavity.

Further, the living tissue (mucous membrane H) can be reliably drawn into the storage tube 22 of the distal unit 15 by virtue of the negative pressure generated by suction means 6, even if the distal unit 15 approaches the living tissue with its axis extending parallel to or inclined to the living tissue. In other words, the living tissue (mucous membrane) can be drawn into and held in the storage tube 22 even if the tissue extends parallel to or is inclined to the axis of the instrument 1. The instrument 1 can therefore serve to cut and sample the target living tissue (mucous membrane).

As mentioned above, the forceps tips 24 and 25, which can open and close, are secured to the distal unit 15 provided at the distal end of the inner tube 11 whose proximal end part is connected to the suction means 6. The forceps tips 24 and 25 can slide on the outer tube 10 as the slider 8 is moved forward or backward. Hence, the blades 24b and 25b of the forceps tips 24 and 25 can cut, without fail, the target mucous membrane H when the slider 8 is moved forward, while a part of the membrane H remains drawn through the opening 27d of the distal frame 27 of the distal unit 15. The instrument can therefore serve to sample a living tissue at any depth, in safety with simple manipulation.

In the present embodiment, the distal frame 27 secured to the distal unit 15 has a rounded distal end 27a, and the blades 24b and 25b of the forceps tips 24 and 25 have rounded parts 24d and 25d, respectively. Namely, the insertion section 2 of the instrument 1 has a rounded distal end. Therefore, the insertion section 2 can be guided through the forceps channel of an endoscope and inserted into a body cavity, without damaging the inner wall of the forceps channel or anything present in the body cavity.

As described above, the outer circumferential surface of the frame 27 is flush with that of the distal pipe 14, and the distal frame 27 functions as a stopper. Thus, the distal unit 15 would not be pulled too much into the distal pipe 14 when the slider is pulled to the proximal end of the operation section 3. The forceps tips 24 and 25 would not be held in the distal pipe 14 too firmly to perform their function.

The opening 27d made in the distal frame 27 is elliptical and is relatively large. Neither the elastic arm 24a of the forceps tip 24 nor the elastic arm 25a of the forceps tip 25 moves to the opening 27d. This enables the instrument 1 to sample a large piece of living tissue.

Furthermore, the operation wire 12 extending in the inner tube 11 would not buckle. This is because the wire 12 moves together with the inner tube when the slider 8 on the operation section 3 is moved in whichever direction. Hence, the operation wire 12 remains extending straight in the inner tube 11.

In addition, a negative pressure to the distal frame 27 can be applied in the distal frame 27 or reduced even if the storage space 22a provided in the suction tube 22 is completely filled with the pieces Ha, Hb, . . . cut from the membrane H. This is because the suction tube 17 arranged in the storage tube 22 has an elliptical opening 19 and side holes 20, maintaining an air passage leading to the distal frame 27 via the side holes 20.

Moreover, not only the storage space 22a is large enough to hold the pieces Ha, Hb, . . . cut from the membrane H. This is because the storage tube 22 has an oblate cross section which is larger than a circular cross section the tube 22 may have. Hence, the space 22a is never filled up with the pieces Ha, Hb, . . . Further, the elastic arms 24a and 25a can be supported on the storage tube 22, since the tube 22 has an oblate cross section and therefore has two flat parts that oppose each other.

Further, since the male-threaded end 21 of the wire coupling 16 is removably inserted in the screw hole 23a of the distal unit 15, the distal unit 15 can be detached from the inner tube 11. It makes it possible to collect the pieces Ha, Hb, . . . easily without providing an independently movable member (e.g., a retractor) in the inner tube 11.

Still further, any piece of membrane H can be cut clean because the blades 24b and 25b completely close the opening 27d of the distal frame 27 when the forceps tips 24 and 25 are moved to their closed positions. No part of the membrane H would be pulled or torn off.

Having saw-tooth edges 24e and 25e respectively, the blades 24b and 25b can bite the membrane H well and cut a piece clean from the membrane H. In addition, the medical instrument 1 can be manufactured easily at low cost since the forceps tips 24 and 25 may be made merely by bending metal or resin strips which have high elasticity.

When the saw-tooth edges 24e of the forceps tip 24 and the saw-tooth edges 25e of the forceps tip 25 meet each other, a shearing force is exerted on the membrane H, reliably cutting a piece from the membrane H. Moreover, a piece can be cut clean off the membrane H because both blades 24b and 25b move forward, sliding on the outer surface of the distal frame 27, and the membrane H is not clamped between either blade and the outer surface of the frame 27.

Having saw-tooth edges 24e and 25e, respectively, the blades 24b and 25b can steadily take hold of the membrane H, never slipping on the membrane H. The blades 24b and 25b can eventually cut a piece from the membrane H without fail.

In the present embodiment, a negative pressure is automatically applied in the inner tube 11 when the forceps tips 24 and 25 are pushed forward, opening the distal end of the distal frame 27. The negative pressure is applied in the inner tube 11 only when necessary, merely by moving the slide 8 to its fore position. Thus, no ON/OFF switch needs to be provided on the suction means 6 to apply the negative pressure and to stop applying the same. This simplifies the manipulation of the medical instrument 1. Furthermore, drying of the pieces Ha, Hb, . . . stored in the storage space 22a can be prevented since the negative pressure is applied, causing an air flow in the space 22a, only when necessary.

Figure 10A:
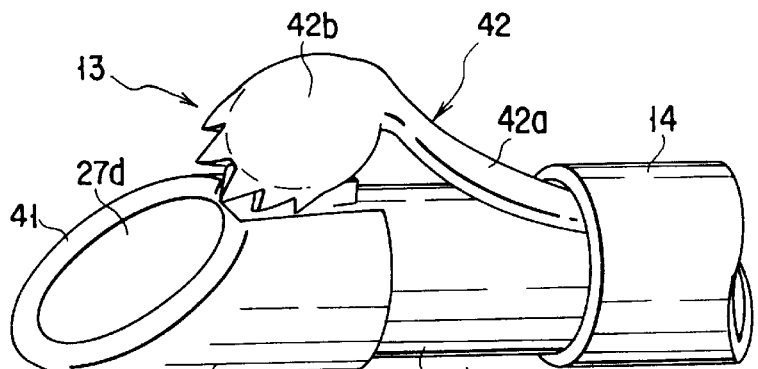
FIG. 10A is a perspective view of the distal end portion of a medical instrument according to a second embodiment of the invention, showing the distal blade held in the opened position.
Figure 10B:
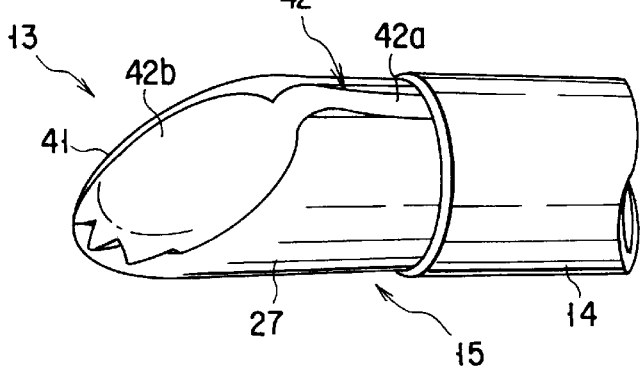
FIG. 10B is a perspective view of the distal end portion of the second embodiment, depicting the distal blade held in the closed position.

A medical instrument for use in combination with an endoscope, which is the second embodiment of the invention, will be described, with reference to FIGS. 10A and 10B. The second embodiment is identical to the first embodiment (FIG. 1A to FIG. 9), except in some respects as will be described below. The components similar or identical to those of the first embodiment are designated at the same reference numerals in FIGS. 10A and 10B and will not described in detail.

In the second embodiment, the distal frame 27 has a distal end 41 inclining to a line extending at right angles to the axis of the distal unit 15. Hence, the opening 27d of the distal frame 27 is elliptical.

Further, only one forceps tip (cutting means) 42 is provided, extending along the upper flat part of the storage tube 22. The forceps tip 42 comprises a straight elastic arm 42a. The proximal end of the arm 42a is secured to the outer circumferential surface of the hollow cylindrical coupling 23 by means of soldering, spot welding, caulking or adhesion, or by means of screws. The elastic arm 42a has a distal portion projecting forward from the distal frame 27 of the storage tube 22. The distal portion of the arms 42a is bent toward the axis of the storage tube 22, forming a blade (cutting portion) 42b. As shown in FIG. 10A, the elastic arm 42a is biased, with the blade 42b located at a distance from the outer circumferential surface of the storage tube 22. The arm 42a supports the blade 42b such that the blade 42b may contact and leave the distal end 41 of the distal frame 27.

When a doctor pulls the slider 8 toward the proximal end of the operation section 3 of the second embodiment, the distal unit 15 is pulled into the distal pipe 14. Then, as shown in FIG. 10B, the blade 42b of the forceps tip 42 completely closes the opening 27d of the distal frame 27, clamping a part of a mucous membrane and cutting this part from the remaining part of the membrane.

The second embodiment is advantageous in that it can sample a larger piece of a membrane than the first embodiment, because the distal frame 27 has an inclined end 41 and, therefore, a larger opening 27a than its counterpart of the first embodiment.

Figure 11:
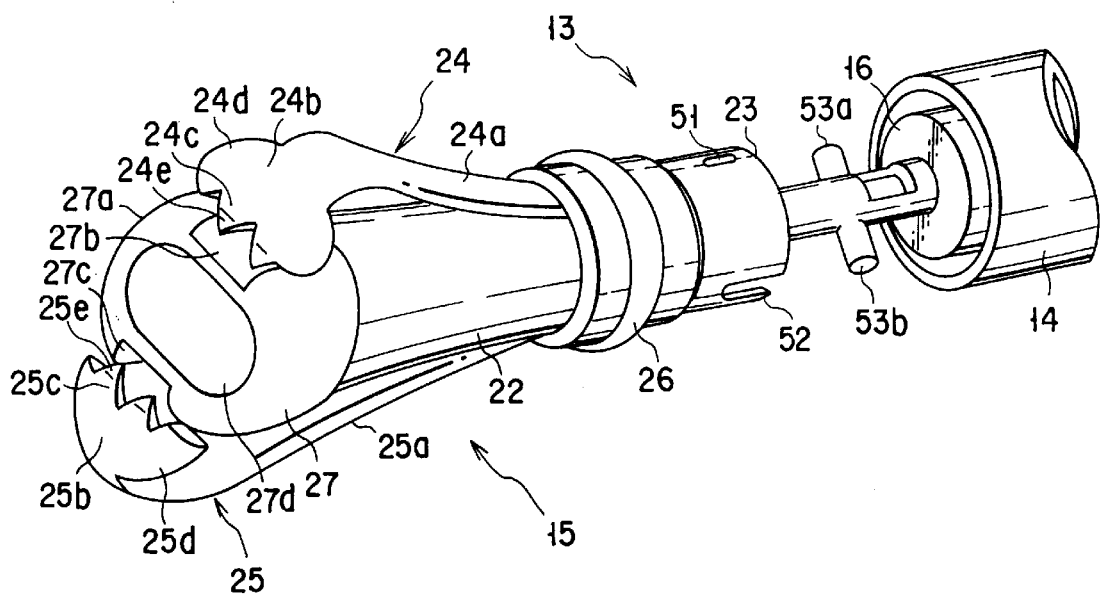
FIG. 11 is a perspective view of the distal end portion of a medical instrument according to a third embodiment of the invention, illustrating the distal unit removed from the distal end of the inner tube.

FIG. 11 shows the third embodiment of the present invention. The third embodiment differs from the first embodiment in only one respect, as will be described below. The components similar or identical to those of the first embodiment are designated at the same reference numerals in FIG. 11 and will not described in detail.

The coupling 23 of the distal unit 15 has a hole 51 and a slit 52, not a screw hole 23a as in the first embodiment. The axis of the hole 51 extends at right angles to the axis of the hollow cylindrical coupling 23. The slit 52 extends parallel to the axis of the coupling 23 and spaced from the hole 51 along the circumference of the coupling 23. As in the first embodiment, a wire coupling 16 is secured to the distal end of the inner tube 11. The wire coupling 16 has two projections 53a and 53b. The projections 53a and 53b are fitted in the hole 51 and the slit 52, respectively, whereby the distal unit 15 is connected to the wire coupling 16.

To collect pieces (not shown) of a mucous membrane from the storage tube 22, the distal unit 15 is pushed forward from the distal pipe 14 and is exposed as a whole. The distal unit 15 is then tilted around the axis of the hole 51, releasing the projection 53b from the slit 52. As a result, the distal unit 15 can be disconnected from the wire coupling 16. After collecting the pieces from the storage tube 22, the distal unit 15 may be connected to the wire coupling 16. To this end, the projection 53a is inserted into the hole 51 of the coupling 23, with the distal unit 15 inclined to the axis of the wire coupling 16. The distal unit 15 is then moved into axial alignment with the wire coupling 16, guiding the projection 53b into the slit 52. The distal unit 15 is thereby connected to the wire coupling 16.

It is easier to insert and pull the projections 53a and 53b into and from the hole 51 and slit 52 than to set and release the male-threaded end 21 of the wire coupling 16 into and from the screw hole 23a of the distal unit 15 in the first embodiment. Hence, the distal unit 15 can be connected and disconnected to and from the wire coupling 16 more quickly in the third embodiment than in the first embodiment.

Figure 12:
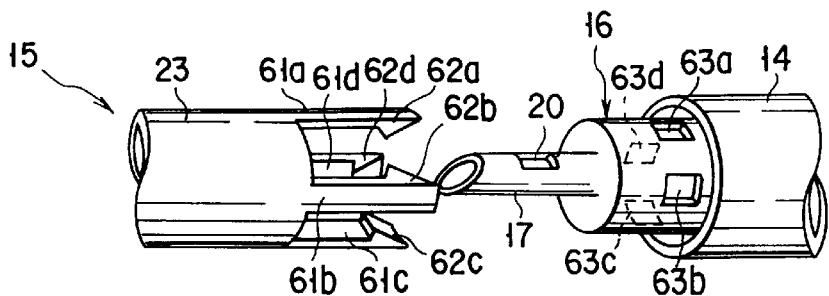
FIG. 12 is a perspective view of a section of a medical instrument according to a fourth embodiment of the invention.

FIG. 12 shows a section of a medical instrument according to the fourth embodiment of the present invention. The fourth embodiment is identical to the first embodiment (FIG. 1A to FIG. 9), except in some respects as will be described below. The components similar or identical to those of the first embodiment are designated at the same reference numerals in FIG. 12 and will not described in detail.

As shown in FIG. 12, a plurality of arms, more correctly four arms 61a to 61d, projects backward from the proximal end of the hollow cylindrical coupling 23 of the distal unit 15. The outer surface of each arm is flush with the outer circumferential surface of the coupling 23. The cylindrical coupling has an outer diameter almost equal to the inner diameter of the distal pipe 14. The arms 61a to 61d have projections 62a to 62d at their free ends, respectively. The projections 62a to 62d extend toward the axis of the distal unit 15. The wire coupling 16 of the inner tube 11 has engagement holes 63a to 63d, which are positioned so as to receive the projections 62a to 62d, respectively.

The wire coupling 16 and the distal unit 15 of the fourth embodiment are disconnected from each other, in order to collect pieces Ha, Hb, . . . which have been cut from a membrane. How the distal unit 15 is disconnected from the wire coupling 16 will be described below.

First, the wire coupling 16 is pushed forward from the distal pipe 14. The arms 61a to 61d of the distal unit 15 are no longer held in the distal pipe 14. The coupling 23 is then pulled away from the pipe 14. As a result, the projections 62a to 62d on the free ends of the arms 61a to 61d slip out of the engagement holes 63a to 63d of the wire coupling 16. The distal unit 15 is thereby disconnected from the wire coupling 16.

In order to connect the distal unit 15 to the wire coupling 16 of the inner tube 11, the distal unit 15 is pushed onto the distal portion of the wire coupling 16. As the unit 15 is so pushed, the arms 61a to 61d are bent away from the axis of the distal pipe 14. As the unit 15 is further pushed, the projections 62a to 62d slip into the engagement holes 63a to 63d of the wire coupling 16. Then, the distal part of the wire coupling 16 is pulled into the pipe 14, the arms 61a to 61d are inserted into the distal pipe 14. Once inserted in the pipe 14, the arms 61a to 61d can no longer bend away from the axis of the pipe 14, and the projections 62a to 62d are held in the engagement holes 63a to 63d. Hence, as long as the arms 61a to 61d remain in the distal pipe 14, the distal unit 15 would not be disconnected from the wire coupling 16.

It is easier to pull and push the distal unit 15 from and into the distal tube 14 to set and release the male-threaded end 21 of the wire coupling 16 into and from the screw hole 23a of the distal unit 15 than in the first embodiment. The distal unit 15 can therefore be connected and disconnected to and from the wire coupling 16 more quickly in the fourth embodiment than in the first embodiment. Like the third embodiment (FIG. 11), the fourth embodiment is advantageous, in this respect, over the first embodiment.

Figure 13:
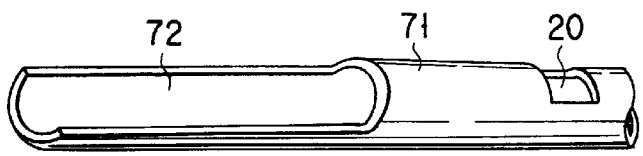
FIG. 13 is a perspective view of a section of a medical instrument according to a fifth embodiment of the present invention.

FIG. 13 shows the suction pipe of a medical instrument according to the fifth embodiment of the present invention. The fifth embodiment is identical to the first embodiment (FIG. 1A to FIG. 9), except the design of the suction pipe. The components similar or identical to those of the first embodiment are designated at the same reference numerals in FIG. 13 and will not described in detail.

The suction pipe 71 used in the fifth embodiment has a sample-storing section 72. As shown FIG. 13. The sample-storing section 72 is shaped like a trough and has a semi-circular cross section. The section 72 extends for a predetermined distance in the axial direction of the suction pipe 71. In the sample-storing section 72, pieces Ha, Hb, . . . cut from a membrane may be stored.

Shaped like a trough, the sample-storing section 72 defines a larger storage space than the suction pipe 17 provided in the first embodiment, which has a distal end cut slantwise and which therefore has an elliptical opening 19 with a major axis inclining to the axis of the pipe 17. Obviously, more pieces Ha, Hb, . . . of a membrane can be stored in the storage space provided in the fifth embodiment than in the storage space 22a provided in the first embodiment.

Figure 14:
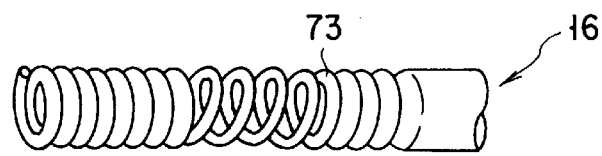
FIG. 14 is a perspective view of a component of a medical instrument according to a sixth embodiment of the invention.

FIG. 14 is a perspective view of the suction pipe of a medical instrument according to the sixth embodiment of the invention. The sixth embodiment is identical to the first embodiment (FIG. 1A to FIG. 9), except that a coil spring is used in place of the suction pipe 17. The components similar or identical to those of the first embodiment are designated at the same reference numerals in FIG. 14 and will not described in detail.

As shown in FIG. 14, the coil spring 73 is secured to the distal end of the wire coupling 16 of the inner tube 11. The space in the coil spring 73 communicates with the space provided in the inner tube 11. Pieces Ha, Hb, . . . cut from a membrane are stored, one after another, into the distal portion of the coil spring 73.

The coil spring 73 will less likely be deformed or damaged when bent, than the suction pipe 17 used in the first embodiment. The instrument 1 according to the sixth embodiment can therefore be handled easily after the distal unit 15 has been removed from it.

Figure 15:
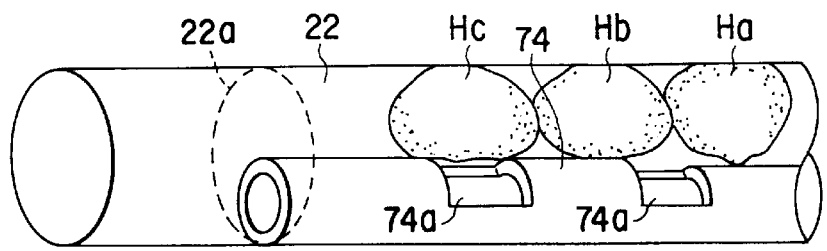
FIG. 15 is a perspective view of the section of a medical instrument according to a seventh embodiment of this invention.

FIG. 15 shows the suction pipe 74 of a medical instrument according to the seventh embodiment of the invention. The seventh embodiment is identical to the first embodiment (FIG. 1A to FIG. 9), except that the suction pipe 74 is used in place of the suction pipe 17 incorporated in the first embodiment. The components similar or identical to those of the first embodiment are designated at the same reference numerals in FIG. 15 and will not described in detail.

As shown in FIG. 15, the suction pipe 74 is positioned in the storage space 22a, not in axial alignment with the storage tube 22 of the distal unit 15. The suction pipe 74 has a plurality of side holes 74a. Pieces Ha, Hb, . . . , cut from a membrane, are stored in the space 22a between the inner circumferential surface of the storage tube 22 and the outer circumferential surface of the suction pipe 74.

Since the suction pipe 74 is not set in axial alignment with the storage tube 22 of the distal unit 15, the storage space 22a is larger than in the first embodiment, wherein the suction pipe 17 is axially aligned with the storage tube 22. Hence, more pieces of tissues can be stored in the space 22a than in the first embodiment.

Figure 16A:
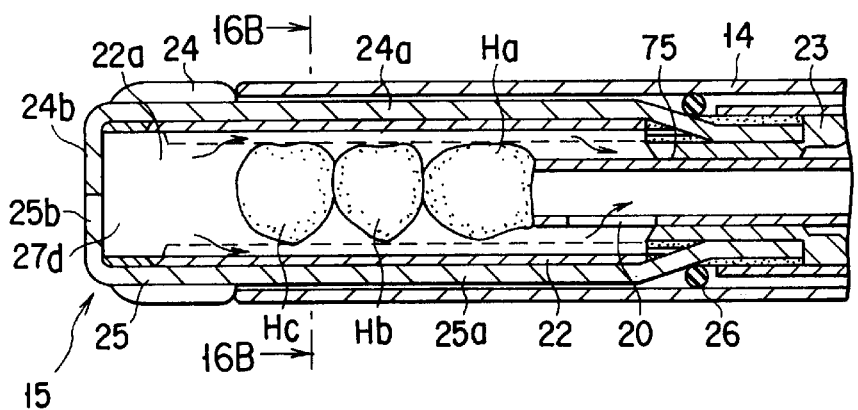
FIG. 16A is a perspective view of the distal end portion of a medical instrument according to an eighth embodiment of the invention, showing pieces of tissue stored in the distal end portion.
Figure 16B:
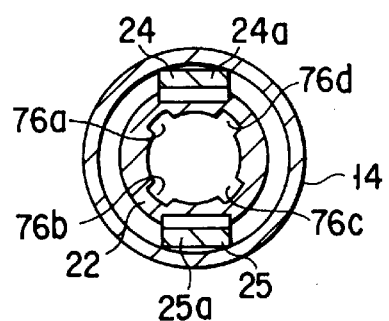
FIG. 16B is a cross-sectional view taken along line 16B—16B in FIG. 16A.

FIGS. 16A and 16B show the distal end portion of a medical instrument according to the eighth embodiment of the invention. The eighth embodiment is identical to the first embodiment (FIG. 1A to FIG. 9), except that the suction pipe 75 is used in place of the suction pipe 17 incorporated in the first embodiment. The components similar or identical to those of the first embodiment are designated at the same reference numerals in FIGS. 16A and 16B, and will not described in detail.

As shown in FIG. 16A, the suction pipe 75 projects into the storage tube 22, for a distance shorter than its counter part 17 projects into the tube 22 in the first embodiment. Further, as shown in FIG. 16B, the storage tube 22 has a plurality of grooves made in its the inner circumferential surface. More correctly, four grooves 76a to 76d extend from one end to the other of the tube 22, parallel to the axis of the tube 22.

After pieces Ha, Hb, . . . , cut from a membrane, have been stored in the storage space 22a provided in the storage tube 22, a negative pressure is applied to the opening 27d of the distal frame 27 from the inner tube 11 through the side holes 20 of the suction pipe 75 and the four grooves 76a to 76d. Since the suction pipe 75 projects into the suction tube 22, but not so long a distance as the suction pipe 17 in the first embodiment, the storage space 22a is larger than in the first embodiment. Hence, more pieces Ha, Hb, . . . of tissues can be stored in the space 22a than in the first embodiment.

Figure 17:
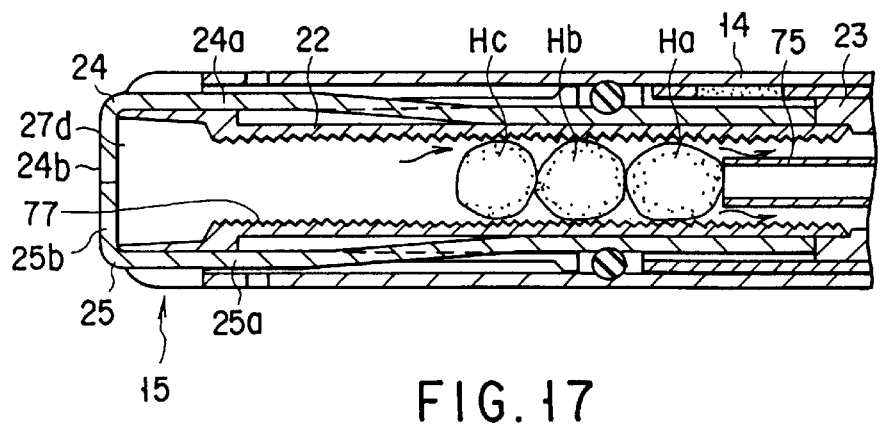
FIG. 17 is a longitudinal sectional view of the distal end portion of a medical instrument according to a ninth embodiment of the invention, showing pieces of tissue stored in the distal end portion.

FIG. 17 depicts the distal end portion of a medical instrument according to the ninth embodiment of the invention. The ninth embodiment is identical to the eighth embodiment (FIGS. 16A and 16B), except that the distal unit 15 is modified in part as will be described below.

As in the eighth embodiment, the suction pipe 75 projects into the storage space 22a of the storage tube 22 provided in the distal unit 15, but not so long a distance as the suction pipe 17 in the first embodiment. As shown in FIG. 17, a helical groove 77 is cut in the inner circumferential surface of the storage tube 22 and extends over all length of the storage space 22a.

In the ninth embodiment, a negative pressure is applied to the opening 27d of the distal frame 27 from the inner tube 11 through the side holes 20 of the suction pipe 75 and the helical grooves 77 after pieces Ha, Hb, . . . , cut from a membrane, have been stored in the storage space 22a provided in the storage tube 22. Since the suction pipe 75 projects into the suction tube 22, but not so long a distance as the suction pipe 17 in the first embodiment, the storage space 22a is larger than in the first embodiment. More pieces Ha, Hb, . . . of tissues can therefore be stored in the space 22a than in the first embodiment.

Figure 18:
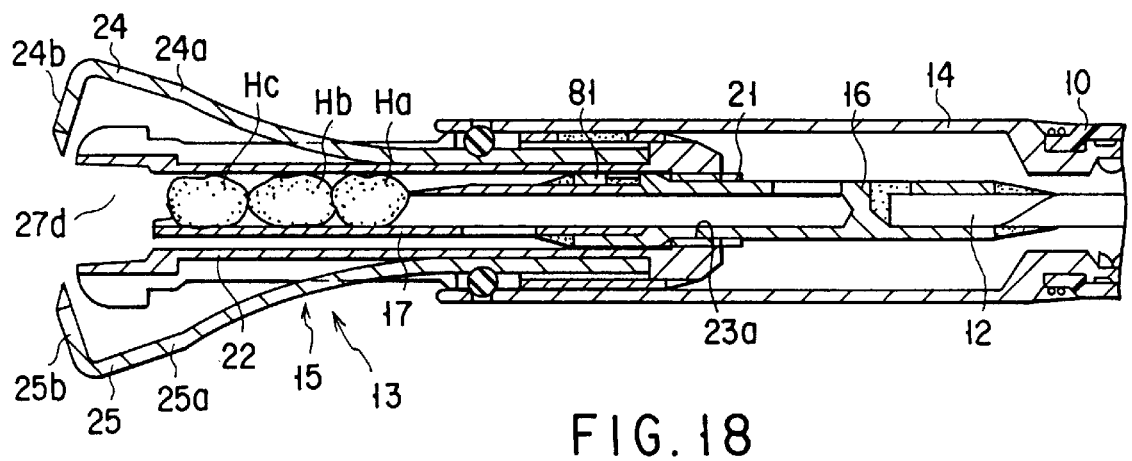
FIG. 18 is a longitudinal sectional view of the distal end portion of a medical instrument according to a tenth embodiment of the invention, depicting the distal unit projecting from the distal pipe.
Figure 19:
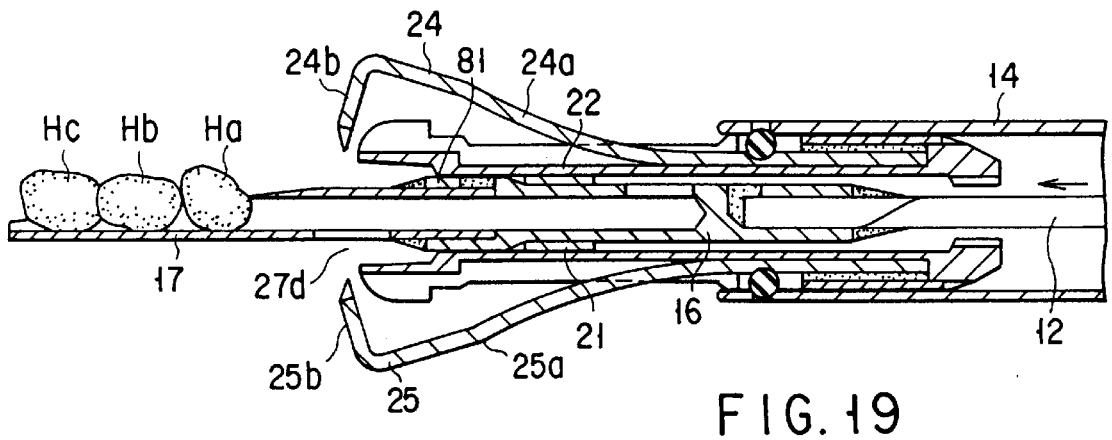
FIG. 19 is a longitudinal sectional view of the distal end portion of a medical instrument according to a tenth embodiment of the invention, showing the suction pipe projecting from the distal unit and holding pieces of tissues.

FIGS. 18 and 19 show the distal end portion of a medical instrument according to the tenth embodiment of this invention. The tenth embodiment is identical to the first embodiment (FIG. 1A to FIG. 9), except that the distal end portion is modified in part as will be described below. The components similar or identical to those of the first embodiment are designated at the same reference numerals in FIGS. 18 and 19, and will not be described in detail.

As shown in FIGS. 18 and 19, a stopper 81 is secured to the male-threaded end 21 of the wire coupling 16. The stopper 81 has an outer diameter larger than the diameter of the screw hole 23a of the distal unit 15. That part of the wire coupling 16 which is more proximal than the male-threaded end 21 has a diameter smaller than the inner diameter of the screw hole 23a. The diameter of the operation wire 12 is also smaller than the inner diameter of the screw hole 23a.

In order to collect pieces Ha, Hb, . . . of a membrane, a doctor pulls the medical instrument 1 from the forceps channel of the endoscope and moves the slider 8 forward, thereby projecting the distal unit 15 from the distal pipe 14. He or she then twists the distal unit 15, releasing the male-threaded end 21 of the wire coupling 16 from the screw hole 23a of the distal unit 15. The doctor further moves the slider 8 forward, the pieces Ha, Hb, . . . are pushed out of the opening 27d of the distal frame 27. Thereafter, the doctor collects the pieces Ha, Hb, . . . , one after another, by using tweezers and filter sheets.

With the tenth embodiment, the distal unit 15 need not be removed from the distal pipe 14 in order to collect the pieces Ha, Hb, . . . . Hence, there is no possibility that the distal unit 15 gets lost.

Moreover, the operation wire 12 and the suction pipe 17 can be used as retractors once the male-threaded end 21 of the wire coupling 16 is pulled out of the screw hole 23a of the distal unit 15. No means for collecting the pieces cut from the membrane needs to be provided independently of the means for operating the cutting means. This simplifies the structure and operation of the medical instrument.

Figures 20A, 20B:
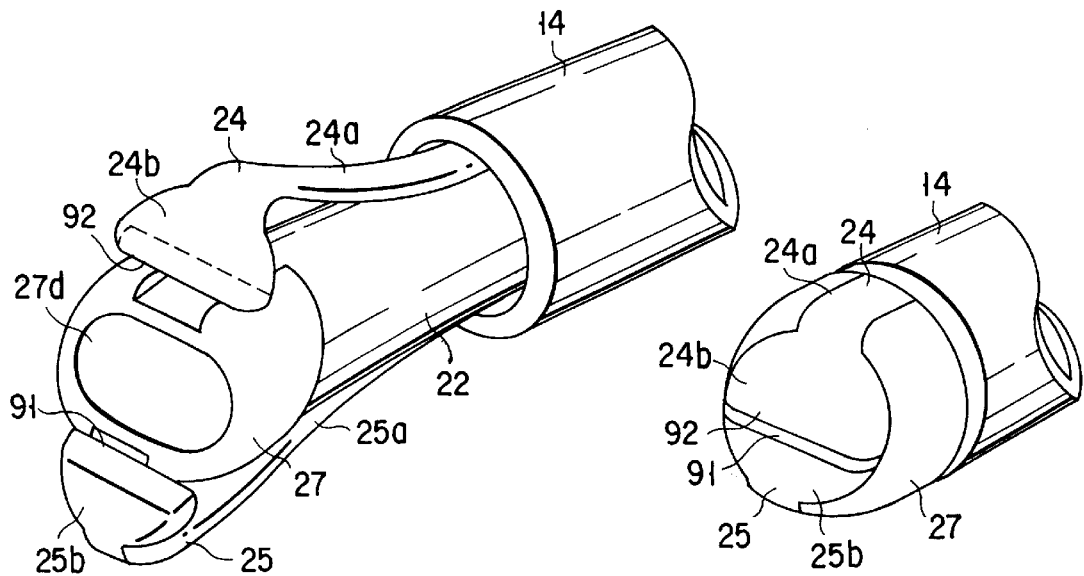
FIG. 20A is a perspective view showing the distal blades of an eleventh embodiment, which are in the opened positions.
FIG. 20B is a perspective view illustrating the distal blades of the eleventh embodiment, which are in the closed positions.

FIGS. 20A and 20B show the distal end portion of a medical instrument according to the eleventh embodiment of the invention. The eleventh embodiment is identical to the first embodiment (FIG. 1A to FIG. 9), except that the distal end portion is modified in part as will be described below. The components of the eleventh embodiment, which are similar or identical to those of the first embodiment, are designated at the same reference numerals in FIGS. 20A and 20B, and will not be described in detail.

As shown in FIGS. 20A and 20B, one of the blades 24b and 25b, for example, the blade 25b of the lower forceps tip 25, has a straight edge 91. The other of the blades 24b and 25b, for example, the blade 24b of the upper forceps tip 24 has a flat contact face 92. The blades 24b and 25b do not have saw teeth as in the first embodiment. Without saw teeth, the blades 24b and 25b are simple in shape and can be made more easily than their counterparts of the first embodiment.

Figures 21A, 21B:
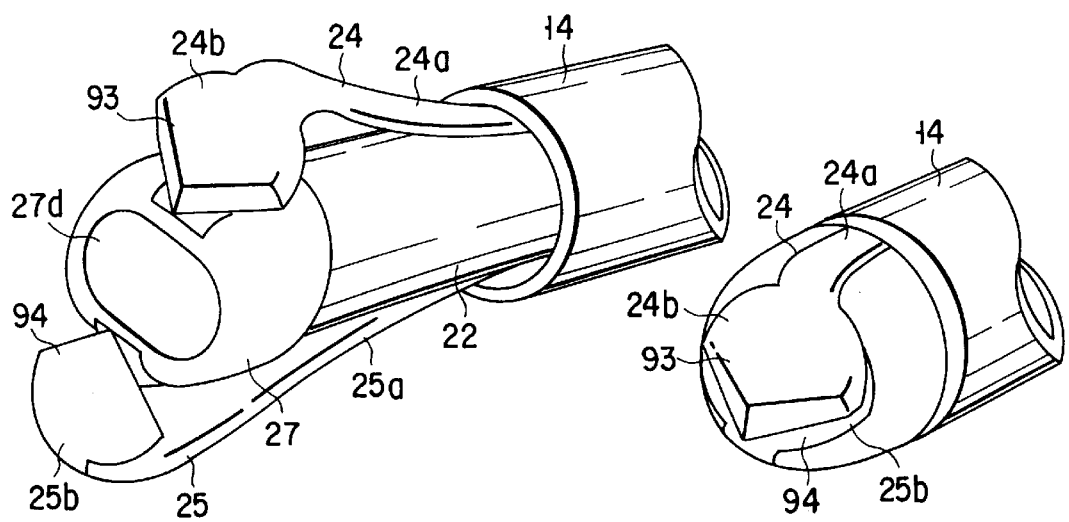
FIG. 21A is a perspective view of the distal end portion of a medical instrument according to a twelfth embodiment of the invention, showing the distal blades which are in the opened positions.
FIG. 21B is a perspective view illustrating the distal blades of the twelfth embodiment, which are in the closed positions.

FIGS. 21A and 21B show the distal end portion of a medical instrument according to the twelfth embodiment of the present invention. The twelfth embodiment is identical to the first embodiment (FIG. 1A to FIG. 9), except that the distal end portion is modified in part as will be described below. The components of the twelfth embodiment, which are similar or identical to those of the first embodiment, are designated at the same reference numerals in FIGS. 21A and 21B, and will not be described in detail.

As shown in FIGS. 21A and 21B, the blade 24b of the upper forceps tip 24 has a shearing edge 93, and the blade 25b of the lower forceps tip 25 similarly has shearing edge 94. As the forceps tips 24 and 25 are moved toward their closed positions, the shearing edge of each blade slides on the outer surface of the distal frame 27. When the forceps tips 24 and 25 reach the closed positions, the shearing edge 93 overlaps the shearing blade 94, in front of the opening 27d of the distal frame 27. In this condition, the shearing edge 94 completely closes the opening 27d of the distal frame 27.

As the forceps tips 24 and 25 are moved toward their closed positions, the inner surface of the shearing edge 93 and the outer surface of the shearing edge 94 come into sliding contact. Hence, the shearing edges 93 and 94 can cut a living tissue, if any, caught in the nip between the inner surface of the shearing edge 93 and the outer surface of the shearing edge 94. Thus, the blades 24b and 25b can cut a piece clean from the living tissue.

FIG. 22 and FIGS. 23A to 23C show a medical instrument according to the thirteenth embodiment of the invention, which is a modification of the first embodiment (FIG. 1A to FIG. 9). The components of the thirteenth embodiment, which are similar or identical to those of the first embodiment, are designated at the same reference numerals in FIG. 22 and FIGS. 23A to 23C, and will not be described in detail.

The thirteenth embodiment has a collection system 101 for collecting pieces Ha, Hb, . . . , without necessity of pulling the medical instrument 1 out of the forceps channel of an endoscope after the pieces Ha, Hb, . . . have been cut from a membrane. The collection system 101 comprises a water-supplying device 102 and a sample-collecting device 103, which are removably connected to the operation section 3 of the instrument 1.

A water-supplying port 104 protrudes from the casing 4 of the operating section 3, at the junction between the insertion section 2 and the operation section 3. A rear port 105 is provided in the proximal end of the casing 4. The distal portion of a slider 106, which is shaped like a hollow cylinder, is inserted in the rear port 105 and can move in the axial direction of the operation section 3. The slider 106 has a collection port 107 in its proximal portion.

As shown in FIGS. 23A to 23C, the inner tube 108 of the sheath 9 of the instrument 1 has its proximal end connected in airtight fashion to the distal portion of the slider 106. The outer tube 109 of the sheath 9 is made of airtight material. The proximal end of the outer tube 109 is connected in airtight fashion to the water-supplying port 104 of the operation section 3. As shown in FIG. 23B, an operation wire 110 is secured to the outer surface of the inner tube 108 by means of adhesion, welding, or the like. A water-supplying lumen 111 is thereby provided in the gap between the inner tube 108 and the outer tube 109, extending over the entire length of the sheath 9. The inner tube 108 has an inner sectional area of at least 1.0 mm$^2$, and the water-supplying lumen 111 has an inner sectional area of 0.5 mm$^2$.

The outer tube 109 is made of flexible material which sufficient compressive strength and tensile strength. It may be, for example, a reinforced tube which is a braided steel cylinder coated, on both inner and outer surfaces, with resin such as polyamide, tetrafluoroethylene, copolymer of tetrafluoroethylene, hexafluoroproplylene, or the like.

A plurality of wires may be provided on the outer tube 109, over the entire length thereof, as on the inner tube 108. The outer tube 109 has an outer diameter of, for example, 2 to 4 mm, so that it may be inserted into the forceps channel of the endoscope.

The inner tube 108 and the operation wire 110 are secured at their distal ends to a rigid tube 112. The rigid tube 112 has an opening 112a at the distal end. The elastic arms 24a and 25a of upper and lower forceps tips 24 and 25 are secured to the outer surface of the rigid tube 112 by means of soldering, spot welding, caulking or adhesion, or by means of screws.

The rigid tube 112 has a hole 113 in its wall. The interior of the outer tube 109 communicates through the hole 113 with the interior of the inner tube 108.

A distal pipe 114 is connected to the distal end of the outer tube 109. A seal member 115, such as an O-ring, is provided in the gap between the rigid tube 112 and the distal pipe 114. Similarly, a seal member 116, such as an O-ring, is provided in the gap between the casing 4 connected to the proximal end of the outer tube 109 and the slider 106 connected to the proximal end of the inner tube 108.

The sample-collecting device 103 has a sample trap 117. The sample trap 117 contains a sample filter 118 and a water tank 119. The sample filter 118 can be removed from the sample trap 117. The water tank 119 is arranged on the bottom of the sample trap 117. A suction means 120 is connected to the sample trap 117, which is connected to the collection port 107 of the casing 4.

The water-supplying device 102 comprises a water tank 121 and a water pump 122. The water tank 121 is connected by a pipe to the water-supplying port 104 of the casing 4. The water pump 122 is connected to the pipe connecting the water tank 121 to the water-supplying port 104. The pump 122 is operated whenever required. A stop valve 123 is provided on the pipe connecting the tank 121 to the port 104, at a position between the water-supplying port 104 and the water pump 122. A finger rest 124 is secured to the operation section 3, in the vicinity of the collection port 107.

Figure 22:
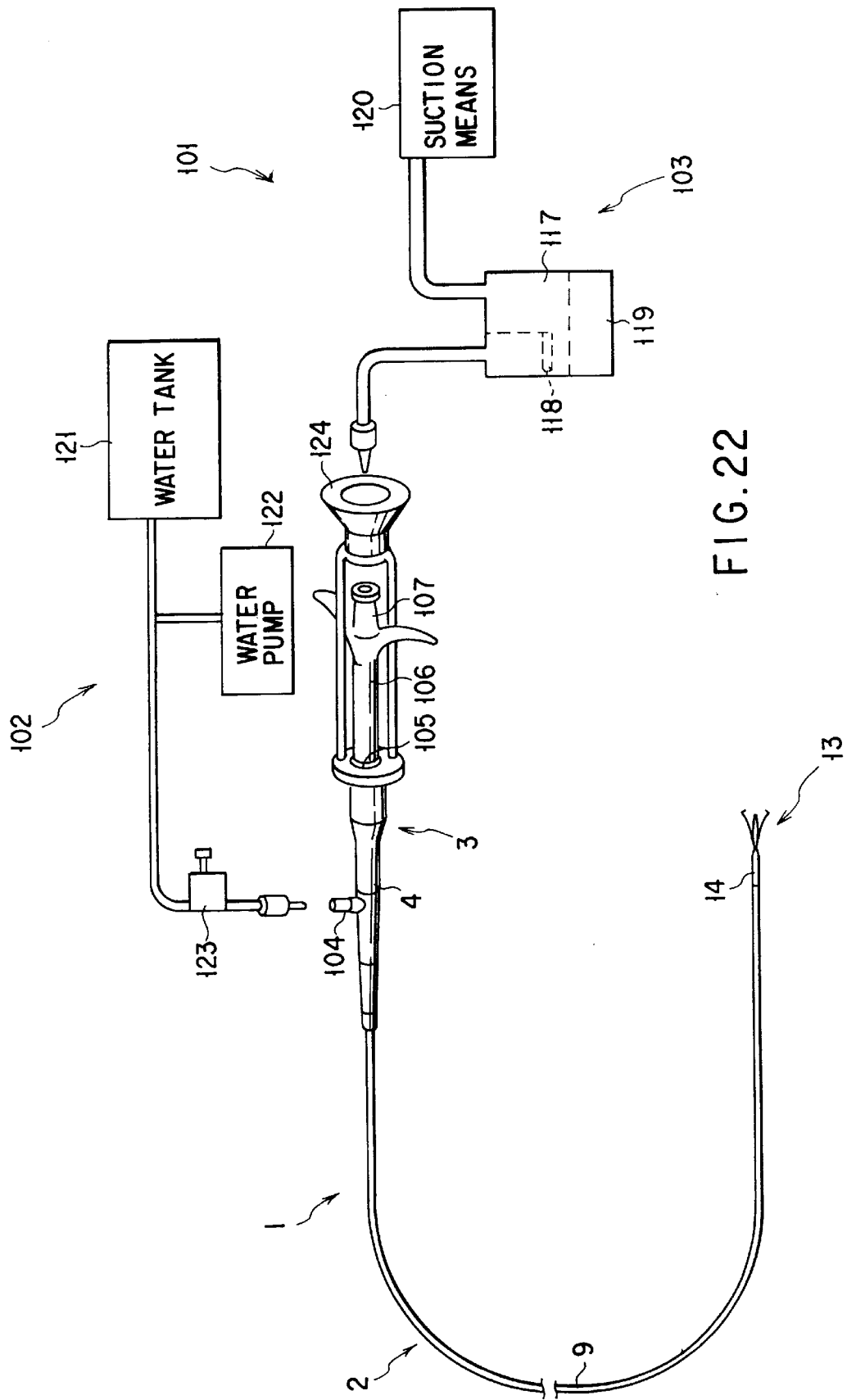
FIG. 22 is a perspective view of a medical instrument for use in combination with an endoscope, which is a thirteenth embodiment of the present invention.

How a doctor manipulates the medical instrument 1 shown in FIG. 22 to sample pieces of tissue will be explained.

First, the water-supplying device 102 is connected to the water-supplying port 104 of the operation section 31 and the sample-collecting device 103 is connected to the collection port 107. Then, the suction means 120 is driven.

Thereafter, the doctor moves the slider 106 toward the proximal end of the operation section 3, thereby pulling the rigid tube 112 into the distal pipe 114 and moving both forceps tips 24 and 25 into their closed positions. The doctor then inserts the insertion section 2 into the patients through the forceps channel of the endoscope, while observing the interior of the body cavity through the endoscope.

The doctor manipulates the instrument 1 to guide the sampling means 13 to a target mucous membrane H existing in the body cavity. (The sampling means 13 is provided at the distal end of the insertion section 2.) When the sampling means 13 reaches the mucous membrane H, the doctor moves the slider 106 toward the distal end of the operation section 3. As a result, the rigid tube 112 is thrust from the distal pipe 114, moving the forceps tips 24 and 25 into their opened positions. The doctor then brings the rigid tube 112 into contact with the target membrane. In this condition, the membrane covers the opening 112a made in the distal end of the rigid tube 112. A part of the membrane is drawn into the rigid tube 112 through the opening 112a, since a negative pressure has been applied to the rigid tube 112 from the suction means 120.

Next, the doctor moves the slider 106 toward the proximal end of the operation section 3, pulling the rigid tube 112 into the distal pipe 114 and moving the forceps tips 24 and 25 into their closed positions. As the forceps tips 24 and 25 are thus moved, they cut that part of the membrane which has been drawn into the rigid tube 112 via the opening 112a. Namely, a piece Ha is cut from the membrane and held in the rigid tube 112, at a position near the opening 112a. The doctor opens the stop valve 123, whereby the negative pressure is applied to the water-supplying lumen 111 and the water-supplying port 104, via the hole 113. Water is drawn from the water tank 121 into the rigid tube 112. At the same time, air flows into the rigid tube 112 via the opening 112a. The piece Ha is flushed with water and air into the inner tube 108 and is ultimately collected at the collection port 107.

The inner tube 108 may be clogged with the piece Ha cut from the membrane. If so, the piece Ha can be flushed into the inner tube 108, merely by driving the water pump 122, thereby supplying more water into the inner tube 108 through the water-supplying lumen 111.

After passing through the collection port 107, the piece Ha is caught by the sample filter 118 in the sample trap 117. At the same time, the water drawn into the sample trap 117 is accumulated in the water tank 119. Thereafter, the sample filter 118 is removed from the sample trap 117, and the piece Ha is collected.

Further, the sequence of operations, described above, is repeated, thereby cutting pieces from membranes and collecting these pieces. After pieces are sampled and collected in desired numbers, the medical instrument 1 is pulled out of the forceps channel of the endoscope.

The medical instrument 1 according to the thirteenth embodiment is advantageous in the following respects.

First, as many pieces as desired can be cut from membranes and subsequently collected, one by one, without necessity of pulling the instrument 1 from the forceps channel of the endoscope. Since the pieces are collected independently of one another, they never happen to mix together in the medical instrument 1. Thus, the order in which the pieces are collected remains clear, and the pieces collected are distinguished from one another.

Further, water can be drawn into the water-supplying lumen 111 from the water tank 121 by applying the negative pressure from the suction means 120. Namely, the water pump need not be driven to supply water from the tank 121 into the lumen 111. This is because the inner tube 108 and the water-supplying lumen 111 have an inner sectional area of at least 1.0 mm$^2$ and an inner sectional area of 0.5 mm$^2$, respectively. Thus, the medical instrument 1 can be simple in structure.

The present invention is not limited to the various embodiments described above. Rather, various changes and modifications can be made, without departing the scope of the present invention.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A medical instrument for use in combination with an endoscope, comprising:
    an elongated insertion section to be inserted into a body through an instrument channel of an endoscope, said insertion section having a sheath comprising an inner tube and an outer tube capable of moving back and forth in an axial direction with respect to the inner tube;
    an operation section connected to a proximal end of the insertion section, connected to a proximal end of said inner tube, and having a suction device for generating a suction force; and
    a sampling unit connected to a distal end of the insertion section and adapted to be driven by operating the operation section, for sampling a part of a living tissue present in the body, said sampling unit comprising a sample receiving chamber provided on a distal portion of said inner tube and having a single opening, through which a living tissue is to be drawn by the suction force applied from said inner tube, and a cutting unit for cutting a part of the living tissue drawn into said sample receiving chamber as said inner tube and said outer tube are moved relative to each other in the axial direction.

2. The medical instrument according to claim 1, wherein said cutting unit has a cutting member comprising a fixed end portion secured to said inner tube and a cutting portion for cutting the living tissue drawn into said inner tube.

3. wherein said suction bypass includes a suction pipe having a side hole and a distal opening open to the distal end of said storage section; and wherein said suction pipe comprises a pipe having a hole therein defining the side hole.

4. The medical instrument according to claim 2, wherein said cutting member moves across the opening of said sample receiving chamber as said outer tube and said inner tube move relative to each other in the axial direction, and closes the opening when said outer tube moves to a distal end of said sample receiving chamber.

5. The medical instrument according to claim 2, wherein said cutting unit comprises a plurality of cutting members.

6. The medical instrument according to claim 5, wherein said cutting members have a flat contact face.

7. The medical instrument according to claim 5, wherein said cutting members move across the opening of said sample receiving chamber to contact each other at a center of said opening, thereby defining a contact line.

8. The medical instrument according to claim 2, wherein said cutting member has a face existing in a same plane as the opening of said sample receiving chamber.

9. The medical instrument according to claim 5, wherein said cutting members have, in a distal end, a recess and a projection, respectively.

10. The medical instrument according to claim 5, wherein said cutting members have a shearing edge and are able to contact each other at a center of said opening.

11. The medical instrument according to claim 1, wherein said sample receiving chamber has rounded parts secured at a distal end thereof.

12. The medical instrument according to claim 11, wherein said rounded parts have a diameter equal to or larger than an outer diameter of said outer tube.

13. The medical instrument according to claim 1, wherein the opening is larger than an inner sectional area of said inner tube.

14. The medical instrument-according to claim 13, wherein the opening of said sample receiving chamber lies in a plane inclined to an axis of the insertion section.

15. The medical instrument according to claim 1, wherein the opening of said sample receiving chamber is oblate.

16. The medical instrument according to claim 1, wherein said cutting unit has an operation wire for moving said inner tube and said outer tube relative to each other in the axial direction, and said operation wire extends through an entire length of the inner tube.

17. The medical instrument according to claim 16, wherein said operation wire is secured along the entire length of the inner tube.

18. The medical instrument according to claim 1, wherein a storage space for storing the living tissue cut by said cutting unit is provided between the proximal end of said inner tube and said suction device.

19. The medical instrument according to claim 18, wherein said insertion section has a water-supplying passage provided outside said inner tube and extending over an entire length of said inner tube.

20. The medical instrument according to claim 1, wherein a storage section for storing the living tissue cut by said cutting unit is provided in a vicinity of a distal end of said inner tube.

21. The medical instrument according to claim 20, wherein a suction bypass is provided which has a distal opening open to a distal end of said storage section and a proximal opening open to a proximal end of said storage section.

22. The medical instrument according to claim 1, wherein a suction bypass is provided which has a suction pipe having a distal opening open to a distal end of said storage section and a proximal opening open to a proximal end of said storage section.

23. The medical instrument according to claim 22, wherein said suction pipe is slideable with respect to said storage section in an axial direction.

24. The medical instrument according to claim 1, wherein said storage section has an elliptical cross section.

25. A medical instrument comprising:
an elongated insertion section to be inserted into a body through an instrument channel of an endoscope, said insertion section having a sheath comprising an inner tube and an outer tube capable of moving back and forth in an axial direction with respect to the inner tube;
an operation section connected to a proximal end of the insertion section, connected to a proximal end of said inner tube, and having a suction device for generating a suction force;
a sampling unit connected to a distal end of the insertion section and adapted to be driven by operating the operation section for sampling a part of a living tissue present in the body, said sampling unit comprising a sample receiving chamber provided on a distal portion of said inner tube and having an opening through which a living tissue is to be drawn by the suction force applied from said inner tube, and a cutting unit for cutting a part of the living tissue drawn into said sample receiving chamber as said inner tube and said outer tube are moved relative to each other in the axial direction; and
a storage section, provided in a vicinity of a distal end of said inner tube, for storing the living tissue cut by said cutting unit;
wherein said storage section has a coupling portion removably connected to said inner tube.

26. The medical instrument according to claim 25, wherein said coupling portion comprises a threaded member removably connected to a proximal end of said storage section and to the distal end of said inner tube.

27. The medical instrument according to claim 25, wherein one of said storage section and said inner tube has projections extending in a radial direction, and the other of said storage section and said inner tube has recesses for holding the projections.

28. The medical instrument according to claim 27, wherein the coupling portion has said recesses, and at least one of said recesses comprises an elongated groove opening to proximal and distal ends of said coupling portion.

29. The medical instrument according to claim 27, wherein said projections are movable in a radial direction.

30. A medical instrument comprising:
an elongated insertion section to be inserted into a body through an instrument channel of an endoscope, said insertion section having a sheath comprising an inner tube and an outer tube capable of moving back and forth in an axial direction with respect to the inner tube;
an operation section connected to a proximal end of the insertion section, connected to a proximal end of said inner tube, and having a suction device for generating a suction force; and
a sampling unit connected to a distal end of the insertion section and adapted to be driven by operating the operation section for sampling a part of a living tissue present in the body, said sampling unit comprising a sample receiving chamber provided on a distal portion of said inner tube and having an opening through which a living tissue is to be drawn by the suction force applied from said inner tube, and a cutting unit for cutting a part of the living tissue drawn into said sample receiving chamber as said inner tube and said outer tube are moved relative to each other in an axial direction;
wherein said cutting unit has a cutting member comprising a fixed end portion secured to said inner tube and a cutting portion for cutting a living tissue drawn into said inner tube; and
wherein:
said inner tube has a suction hole,
said operation section has a suction casing provided at a proximal end of said outer tube and outside said inner tube and having an airtight chamber connected to said suction device, and
said cutting member opens the opening of said sample receiving chamber while remaining in said airtight chamber and closes the opening of said sample receiving chamber while remaining outside said airtight chamber.

31. The medical instrument according to claim 30, wherein:
said suction casing has a plurality of airtight chambers independent of one another, including a first airtight chamber and a second airtight chamber,
said suction device is connected to said first airtight chamber, and
said cutting member opens the opening of said sample receiving chamber while remaining in said first airtight chamber, and closes the opening of said sample receiving chamber while remaining in said second airtight chamber which is not connected to said suction device.

32. A medical instrument for use in combination with an endoscope, comprising a flexible sheath, a suction lumen provided in the flexible sheath, a suction device which generates a suction force, said suction device being connected to a proximal end of the suction lumen, a cutting unit provided at a distal end of the flexible sheath, and a storage section provided in a proximal end of the cutting unit, for storing living tissue,
wherein said storage section has a suction bypass which has a distal opening open to a distal end of said storage section and a proximal opening open to a proximal end of said storage section;
wherein said suction bypass includes a suction pipe having a side hole and a distal opening open to the distal end of said storage section; and
wherein said suction pipe is made of a coil spring.

33. A medical instrument for use in combination with an endoscope, comprising a flexible sheath, a suction lumen provided in the flexible sheath, a suction device which generates a suction force, said suction device being connected to a proximal end of the suction lumen, a cutting unit provided at a distal end of the flexible sheath, and a storage section provided in a proximal end of the cutting unit, for storing a living tissue,
wherein said storage section has a suction bypass which has a distal opening to a distal end of said storage section and a proximal opening open to a proximal end of said storage section; and wherein said storage section has a helical suction groove in an inner surface thereof.

34. A medical instrument for use in combination with an endoscope, comprising a flexible sheath, a suction lumen provided in the flexible sheath and having a suction opening in a distal portion, suction device which generates a suction force, said suction device being connected to a proximal end of the suction lumen, and a cutting unit provided at a distal end of the flexible sheath, wherein:
said suction lumen has a suction hole in the proximal end thereof;
said flexible sheath has, in a proximal end, a suction casing located outside said suction lumen and having a plurality of airtight chambers, at least one of which is connected to said suction device; and
said suction hole remains in the at least one airtight chamber which is connected to said suction device, while said cutting unit keeps opening the opening, and which remains outside said at least one airtight chamber which is connected to said suction device, while said cutting unit keeps closing at least a part of the opening.

35. The medical instrument according to claim 34, wherein said flexible sheath has a water-supplying passage.

36. The medical instrument according to claim 35, wherein said water-supplying passage has a sectional area of at least 0.5 mm$^2$.

37. The medical instrument according to claim 34, wherein said flexible sheath has such an outer diameter so as to be inserted into the endoscope.

38. The medical instrument according to claim 34, wherein said suction lumen has a sectional area of at least 1.0 mm$^2$.

39. The medical instrument according to claim 34, wherein:
said suction casing has a plurality of airtight chambers independent of one another; and
said suction hole remains in the at least one airtight chamber which is connected to said suction device, while said cutting unit keeps opening the opening, and which remains in another airtight chamber non-connected to said suction device, while said cutting unit keeps closing at least a part of the opening.

* * * * *